(12) United States Patent
Toivonen et al.

(10) Patent No.: US 9,857,345 B2
(45) Date of Patent: Jan. 2, 2018

(54) METHOD FOR MEASURING TEMPERATURE, MOLECULAR NUMBER DENSITY, AND/OR PRESSURE OF A GASEOUS COMPOUND FROM A THERMAL DEVICE, AND A THERMAL SYSTEM

(71) Applicant: VALMET POWER OY, Tampere (FI)

(72) Inventors: Juha Toivonen, Tampere (FI); Antti Aalto, Tampere (FI); Matti Sarén, Kajaani (FI); Juha Roppo, Lempäälä (FI)

(73) Assignee: VALMET TECHNOLOGIES OY, Espoo (FI)

( * ) Notice: Subject to any disclaimer, the term of this patent is extended or adjusted under 35 U.S.C. 154(b) by 544 days.

(21) Appl. No.: 14/554,902

(22) Filed: Nov. 26, 2014

(65) Prior Publication Data
US 2015/0144297 A1    May 28, 2015

(30) Foreign Application Priority Data
Nov. 26, 2013 (FI) ...................................... 20136181

(51) Int. Cl.
*G01N 25/00* (2006.01)
*G01K 11/00* (2006.01)
(Continued)

(52) U.S. Cl.
CPC ......... *G01N 33/0036* (2013.01); *F23N 5/022* (2013.01); *F23N 5/082* (2013.01);
(Continued)

(58) Field of Classification Search
USPC .......................................... 374/45, 120, 161
See application file for complete search history.

(56) References Cited

U.S. PATENT DOCUMENTS 4,493,553 A * 1/1985 Korb ........................ G01D 5/26
356/43
5,111,055 A    5/1992 Fima
(Continued)

FOREIGN PATENT DOCUMENTS

EP    2 587 154 A1    5/2013
JP    A-2001-33018    2/2001

OTHER PUBLICATIONS

Apr. 7, 2015 Extended Search Report issued in European Patent Application No. 14397536.5.
(Continued)

*Primary Examiner* — Mirellys Jagan
(74) *Attorney, Agent, or Firm* — Oliff PLC

(57) ABSTRACT

A method for measuring, from a thermal device, temperature, molecular number density, and/or pressure of a gaseous compound as function of distance, the gaseous compound absorbing at least some light. The method comprises generating, for a first wavelength band and a second wavelength band, a pulse sequence comprising a light pulse or light pulses, guiding the pulse sequence into the thermal device, and measuring, as function of time, the intensity of the scattered light at the first wavelength band and at the second wavelength band. The method further comprises determining information indicative of the differential absorption between the two wavelengths bands using measured intensities and determining the temperature, the molecular number density, and/or the pressure of the gaseous compound using the information indicative of the differential absorption between the two wavelengths bands. A thermal system arranged to carry out the method.

18 Claims, 6 Drawing Sheets

(51) Int. Cl.
  *G01N 33/00* (2006.01)
  *G01L 11/02* (2006.01)
  *G01S 17/88* (2006.01)
  *G01N 21/51* (2006.01)
  *F28F 27/00* (2006.01)
  *G01N 21/39* (2006.01)
  *G01N 21/49* (2006.01)
  *F23N 5/02* (2006.01)
  *F23N 5/08* (2006.01)
  *G01N 21/17* (2006.01)

(52) U.S. Cl.
  CPC .............. *F28F 27/00* (2013.01); *G01K 11/00* (2013.01); *G01L 11/02* (2013.01); *G01N 21/39* (2013.01); *G01N 21/49* (2013.01); *G01N 21/51* (2013.01); *G01S 17/88* (2013.01); *F23N 2025/04* (2013.01); *F23N 2025/08* (2013.01); *G01N 2021/1734* (2013.01); *G01N 2201/0697* (2013.01); *G01N 2201/06113* (2013.01)

(56) References Cited

U.S. PATENT DOCUMENTS 5,667,304 A    9/1997   Gelbwachs
2007/0109528 A1   5/2007   Caldwell et al.

OTHER PUBLICATIONS

Sanders, "Wavelength-Agile Fiber Laser Using Group-Velocity Dispersion of Pulsed Super-Continua and Application to Broadband Absorption Spectroscopy," *Appl. Phys. B*, 2002, pp. 799-802.

Ere-Tassou et al., "Femtosecond Laser Source for Real-Time Atmospheric Gas Sensing in the UV—Visible," *Optics Communications*, 2003, pp. 215-221.

Office Action issued in Finnish Application No. 20136181 dated Aug. 20, 2014.

* cited by examiner

METHOD FOR MEASURING TEMPERATURE, MOLECULAR NUMBER DENSITY, AND/OR PRESSURE OF A GASEOUS COMPOUND FROM A THERMAL DEVICE, AND A THERMAL SYSTEM

FIELD OF THE INVENTION

The invention relates to measuring temperature, molecular number density, and/or pressure of a gaseous compound using electromagnetic radiation, such as light. The invention relates to measuring temperature, molecular number density, and/or pressure of a gaseous compound using collimated light pulses. The invention relates to measuring temperature, molecular number density, and/or pressure of a gaseous compound as function of distance from a location in a direction. The invention relates to measuring temperature, molecular number density, and/or pressure profile in a thermal device. The invention relates method for controlling thermal devices.

BACKGROUND

The operation of thermal devices depend on the temperature distribution inside the thermal device. Temperature can be measured e.g. by inserting thermal sensors in various locations in the thermal device. However, the maintenance of multiple temperature sensors is a significant burden for the operator of the thermal device. The thermal device may refer e.g. to a boiler, a pyrolysis reactor, a torrefaction reactor, or a gasifier.

Prior art solutions include also some acoustical and optical methods for determining temperature inside a thermal device. However, these methods can not as such, by using only a single opening, be used to measure a profile of temperature and/or molecular number density inside a thermal device. Moreover these methods can not as such be used to measure a three dimensional profile of the aforementioned quantities.

SUMMARY OF THE INVENTION

An electromagnetic method for measuring one, two, or all of
- the temperature
- the molecular number density, and
- the pressure, of a gaseous compound is disclosed. As the concentration depends on the temperature, the molecular number density, and the pressure, also the concentration can be measured. As the method is electromagnetic, the devices can be located outside of a thermal device; while the method provides information from inside the thermal device. This reduces the maintenance needs of the measurement equipment.

Moreover, the method provides for the aforementioned information as function of distance in a prescribed direction. By varying the direction, a spatial profile of at least one of the aforementioned variables can be obtained through only one optical inlet. By varying the direction in non-parallel planes (e.g. orthogonal planes), a three dimensional profile is obtainable.

An embodiment of the method comprises
selecting a first wavelength band and a second wavelength band using information on the spectrum of the absorption cross section of the gaseous compound and/or the temperature dependence thereof,
generating, for the first wavelength band and the second wavelength band, a pulse sequence comprising a light pulse or light pulses,
guiding the pulse sequence, from a location, in a first direction, into a thermal device, wherein the thermal device surrounds some gaseous mixture, the gaseous mixture comprising the gaseous compound and scattering particles, whereby
  molecules of the gaseous compound absorb at least part of the light pulse or at least one of the light pulses, and
  particles of the gaseous mixture scatter at least part of the light pulse or the light pulses at various moments of time at least to scattered light; the method comprising
measuring, as function of time, the intensity of the scattered light at the first wavelength band,
measuring, as function of time, the intensity of the scattered light at the second wavelength band,
determining information indicative of the differential absorption between the two wavelengths bands using the intensity of the scattered light at the first wavelength band and the intensity of the scattered light at the second wavelength band, and
determining the temperature, the molecular number density, and/or the pressure of the gaseous compound as function of the distance from the location in the first direction using the information indicative of the differential absorption between the two wavelengths bands.

Other features of the method are discussed in the dependent claims 2 to 12.

The method can be performed using a device in connection with a thermal device. An embodiment of such an arrangement comprises
a thermal device comprising at least a member limiting a space, the member having an optical inlet, wherein, in use, the space is arranged to contain some gaseous mixture comprising some gaseous compound and scattering particles, the gaseous molecules of the compound absorbing at least some light at least at a first wavelength band or a second wavelength band and the scattering particles scattering at least some light at least at a first wavelength band or a second wavelength band; the system comprising
a light pulse source arrangement arranged to generate, for the first wavelength band and the second wavelength band, a pulse sequence comprising a light pulse or light pulses,
means for guiding, from a location, to a first direction, the pulse sequence into the space through the optical inlet, whereby molecules of the gaseous compound absorb at least part of at least one of the light pulses and the particles of the gaseous mixture scatter at least part of the light pulse or the light pulses to scattered light,
a detector arrangement arranged to measure, as function of time, the intensity of the scattered light at the first wavelength band and at the second wavelength band, and
a processing unit for determining the temperature, the molecular number density, and/or the pressure of the gaseous compound as function of the distance from the location in the first direction using the measurement results of the detector by determining information indicative of the differential absorption between the two wavelengths bands using the information provided by the detector arrangement.

Other features of the thermal device are disclosed in dependent claims 13 to 17.

DETAILED DESCRIPTION OF EMBODIMENTS

Figure 1A:
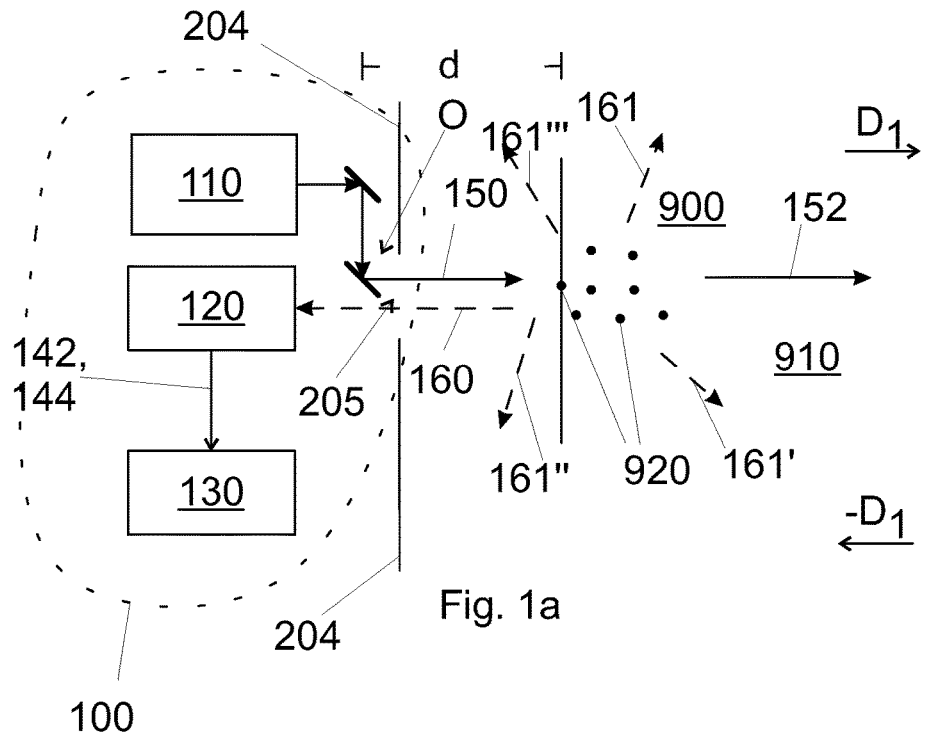
FIG. 1a shows a device and a method for measuring temperature, molecular number density, and/or pressure of a gaseous compound as function of distance at a first instance of time

In this description, the term "molecular number density" refers to a quantity N/V, wherein N is the number of molecules of a gaseous compound in a volume V. A method for measuring temperature, molecular number density, and/or pressure of the gaseous compound as function of distance will be discussed with reference to FIGS. 1a and 1b. As will become clear, the method is particularly suitable for measuring the aforementioned properties from an operating thermal device. A thermal device comprises members (such as walls or ceiling) limiting a space, i.e. an interior of the thermal device. The gaseous compound 910 is comprised by a gaseous mixture 900. In a typical use of a thermal device, the gaseous mixture is arranged in the space of the thermal device. The gaseous mixture 900 can be referred to as an aerosol, since, as will be evident, the gaseous mixture comprises at least some of the gaseous compound 910 and particles 920 that scatter light. Moreover, the gaseous mixture 900 may comprise also other gaseous compounds than the one being measured (i.e. the gaseous compound 910). As is well known from the optical properties of gases, the gaseous compound 910 attenuates light propagating through it, wherein the amount of attenuation depends e.g. on the wavelength of the light, the distance travelled by the light, and the molecular number density of the gaseous compound 910 in the gaseous mixture 900. This attenuation is in particular due to absorption to the molecules of the gaseous compound 910. In addition, the particles 920 scatter light hitting the particles.

In this description, the word "light" is used for electromagnetic radiation in the wavelength range from 300 nm to 25 µm. Thus the term "light" covers ultraviolet (UV) light (i.e. radiation) and also covers infrared (IR) light (i.e. radiation). In particular, light from the near infrared, having the wavelength from 0.8 µm to 2.5 µm, can be used. Preferable wavelengths will be discussed in more detail below.

The method is based on measuring the absorption at at least two wavelengths bands, and by using this information, determining at least one of temperature, molecular number density, and pressure. If only two wavelength bands are used, only one quantity can be measured.

The absorption depends on the distance traveled by light, the absorption cross section of the molecules of the gaseous compound, the wavelength of the light, and the molecular number density of the molecules of the gaseous compound. The absorption further depends on temperature via the temperature dependence on the optical properties of the gaseous compound 910, the absorption cross section in particular. The absorption further depends on pressure via the pressure dependence on the optical properties of the gaseous compound 910, the absorption cross section in particular. These features of the gaseous compound 910 are employed by measuring how much the light is absorbed by the molecules of the gaseous compound 910. This feature yields information on at least one of temperature, molecular number density, and pressure. As will become clear, the method is especially suitable for measuring at least one of temperature and molecular number density. Moreover, as will become clear, the method is especially suitable for measuring both the temperature and the molecular number density.

The gaseous mixture 900 further comprises particles 920. When light hits the particles 920, at least part of the light scatters. In particular, at least part of the light scatters back to the opposite direction. This is another property of the gaseous mixture that is employed in various embodiments of the invention. Thus, the method is particularly suitable for measuring the temperature and/or the molecular number density of a gaseous compound 910 from a gaseous mixture 900 comprising scattering particles 920. Typically thermal processes, such as combustion, produce a gaseous mixture 900 that comprises suitable amounts of scattering particles 920 for the present method.

The gaseous mixture 900 may be surrounded by a vessel or by a member or members (e.g. wall 204) of a thermal device. A wall 204 of the vessel or the device is shown in FIG. 1a, even if—for the measurement principle—such wall needs not be present. In case a member (e.g. wall 204) is present, the member comprises at least one optical inlet 205 for letting an optical pulse 150 in to the space comprising the gaseous mixture 900. As is clear, the optical inlet 205 may also serve as an optical outlet for letting out a scattered optical pulse 160 (i.e. a backscattered pulse 160) as will be discussed later. However, in principle the scattered optical pulse 160 may be led out via another optical outlet. The optical inlet may be a hole or a window. The window is at least partly transparent to the light used.

An aspect of various embodiments of the method, not related to the gaseous compound to be measured, is that relatively short light pulses are used. Therefore, when the intensity of scattered light is measured as function of time, the distance that the light pulse has propagated can be solved using the time of flight of the light pulse, since the velocity of light is known. The spatial accuracy depends on e.g.

the temporal duration of the light pulse,
the pulse response of the detector arrangement 120, and
the frequency by which the intensity is recorded (in sense of samples per second; not the frequency of the light detected).

The pulse response of the detector arrangement 120 characterizes the delay (i.e. time) between the instances of light hitting a photodetector of the detector arrangement 120, and a signal rise at the output or the detector arrangement 120. The detector arrangement 120 may comprise, in addition to the photodetector(s), other electronics, such as signal amplifies and/or analog to digital converters. In general, the pulse response of the detector arrangement may be less than the duration of the light pulse.

FIG. 1a shows an embodiment of a method and a device 100 for measuring temperature, pressure, and/or molecular number density of a gaseous compound as function of distance. The gaseous compound 910 attenuates at least some light; in particular light having a first wavelength $\lambda_1$ and/or a second wavelength $\lambda_2$. Herein the first wavelength $\lambda_1$ belongs to a first wavelength band $\Lambda_1$ and the second wavelength $\lambda_2$ belongs to a second wavelength band $\Lambda_2$. The wavelength bands may be narrow, such as in case of a regular laser having the band width of e.g. less than 1 nm, or the wavelength bands may be wide, such as in case of a supercontinuum laser having the band width of e.g. more than 5 nm.

The method comprises selecting the wavelength bands ($\Lambda_1, \Lambda_2$) using information on the spectrum of the absorption coefficient of the gaseous compound to be measured, as will be detailed later.

The method further comprises generating a light pulse 150 for the first wavelength band $\Lambda_1$. In the method, the same light pulse may serve also as a light pulse for the second wavelength band $\Lambda_2$. This may be the case, if a light source having a wide spectrum is used. This may also be the case, wherein at least two (e.g. a multiple of) pulses from narrow band light sources are optically combined to a single pulse. However, it is also possible to generate another, subsequent, light pulse for the second wavelength band $\Lambda_2$. The light pulse or the combination of light pulses will be referred to as a pulse sequence. The pulse sequence comprises at least one light pulse, i.e. a light pulse or subsequent light pulses. The pulse sequence is a sequence for at least the two wavelength bands, i.e. a single pulse of the pulse sequence covers both (or more generally all) the wavelength bands, or one light pulse of the pulse sequence is for one wavelength band, and another light pulse of the pulse sequence is for another wavelength band.

The pulse sequence is generated in a light pulse source arrangement 110. The light pulse source arrangement may comprise one or several light pulse sources for generating the pulse sequence. The light pulse source arrangement 110 may comprise at least two lasers. Each laser may generate narrow band light pulses, such as essentially monochromatic light sub-pulses, and by combining the sub-pulses of various lasers, a light pulse 150 as described can be produced. Light sub-pulses can be combined by using reflectors and/or wavelength sensitive reflectors as known in the art. Preferably, for reasons to be discussed, the light pulse source arrangement 110 comprises a supercontinuum laser source. A supercontinuum laser source produces light pulses having a continuous, relatively wide, spectrum and relatively high energy. The light pulse from a supercontinuum source may serve as the light pulse for the first wavelength band and the pulse for the second wavelength band. The band width of a supercontinuum laser light pulse may be from 60 nm to 5000 nm, typically from 500 nm to 2000 nm. In the present method, preferably relatively narrow band supercontinuum source is used, whereby the band width of the light source is preferably less than 500 nm, and more than 60 nm, as discussed above. A supercontinuum source may produce continuous light. Typically a supercontinuum laser light pulse source produces pulses with a duration from 10 fs to 10 ns. Due to spatial accuracy requirements, preferably the duration of the pulse if from 0.1 ns to 10 ns (providing the spatial resolution on 1.5 cm to 1.5 m), such as from 0.3 ns to 3 ns, such as about 1 ns. This applies also to embodiments, wherein regular lasers are used. Typically a supercontinuum laser light pulse has the energy of from 10 nJ to 100 μJ. This applies also to embodiments, wherein regular lasers are used.

The method comprises guiding the pulse sequence (comprising the light pulse 150), from a location O (FIG. 1a), in a first direction $D_1$, into a thermal device, wherein the thermal device surrounds the gaseous mixture 900, the gaseous mixture 900 comprising the gaseous compound 910 absorbing at least some of the pulse sequence and the particles 920 scattering least some of the pulse sequence. As discussed above, the molecules of the gaseous compound 910 absorb at least part of the light pulse 150, thereby attenuating the light pulse. When the attenuated light pulse hits a particle 920 in the gaseous mixture 900, the particle 920 of the gaseous mixture scatters at least part of the light pulse 150 to at least a scattered light pulse 160. In particular, the particle 920 of the gaseous mixture scatters at least part of the light pulse 150 back to a reverse direction $-D1$; this part being referred to as the backscattered light pulse 160. Moreover, the molecules of the gaseous compound 910 absorb at least part of the scattered light pulse 160. As absorption may depend on wavelength, the molecules of the gaseous compound 910 do not necessarily absorb all the wavelengths of the light pulse 150 or the scattered light pulse 160. As all the pulses of the pulse sequence will be scattered, the scattered pulses can be commonly referred to as scattered light. The backscattered pulses can be commonly referred to as backscattered light.

As shown in FIG. 1a, the particle 920 may scatter the light pulse 150 to also other scattered pulses, such as the scattered pulse 161. However, to simplify the equipment, preferably the scattered light pulse 160 is measured in only one detector arrangement 120 (possibly comprising several photodetectors, as will be discussed). Thus, the other scattered pulses 161, 161', 161", and 161'" need not be measured. Moreover, to simplify the analysis, preferably the backscattered light (comprising e.g. the pulse 160) is measured. This will discussed in more detail later.

When the light pulse 150 hits a particle 920, a part 152 of the light pulse 150 is not scattered. E.g. the cross-sectional area of the light pulse 150 may be larger than the cross sectional area of the particle. Typically, the light pulse has a circular cross-section. Preferably the diameter of the cross-section of the light pulse is from 1 mm to 500 mm. In consequence, typically, the cross-sectional area of a light pulse, optionally non-circular in cross-section, is from 0.8 mm$^2$ to 2000 cm$^2$. With reference to FIG. 1 b, the part 152 of the light pulse will be scattered from another particle 920 slightly later. Therefore, the scattered light pulse 160 that is observed, is a result of multiple subsequent scattering events, each of these scattering events occurring at a different distance from the first location O in the first direction $D_1$. Therefore, in the method, particles 920 of the gaseous mixture 900 scatter at least part of the light pulse 150 at various moments of time at least to a scattered light pulse 160.

The corresponding device 100 comprises means for guiding, from a location O in a first direction $D_1$, the pulse sequence into the space of the thermal device through the optical inlet 205. Thereby the molecules of the gaseous compound absorb at least part of at least one of the light pulses (the pulse 150 and the other pulse optionally generated); and the a particles of the gaseous mixture scatter at least part of the light pulse or the light pulses to the aforementioned scattered light, such as backscattered light.

The method comprises measuring, as function of time, the intensity of the scattered light at the first wavelength band $\Lambda_1$; and measuring, as function of time, the intensity of the scattered light at the second wavelength band $\Lambda_2$. In particular, the method comprises measuring, as function of time, the intensity of the scattered light pulse 160 at the first wavelength band $\Lambda_1$. Provided that one pulse for both wavelength bands has been generated, the method further comprises measuring, as function of time, the intensity of the scattered light pulse 160 at the second wavelength band $\Lambda_2$. Provided that another pulse has been generated for the second wavelength band, the method further comprises measuring, as function of time, the intensity of the scattered other light pulse at the second wavelength band $\Lambda_2$. The device 100 comprises a detector arrangement 120 for measuring the aforementioned intensities. The device 100 comprises a detector arrangement 120 arranged to measure these intensities. The device may comprise exactly one detector arranged to measure both these intensities. The device may comprise a first detector arranged to measure the intensity at the first band and a second detector arranged to measure the intensity at the first band. The detector arrangement 120 may comprise a photodetector and collection optics to collect the scattered pulse to the photodetector.

The detector arrangement 120 may have is own wavelength dependent response function. Preferably the detector arrangement 120 is arranged to detect at least the whole first wavelength band $\Lambda_1$ and the whole second wavelength band $\Lambda_2$. If this is not the case, the bandwidth of the detector arrangement 120 needs to be taken into account when selecting the wavelength bands $\Lambda_1$ and $\Lambda_2$. As for later discussion, when the detector arrangement 120 is arranged to detect a wavelength band $\Lambda_{11}$ and the pulse for the first wavelength band comprises photons from a wavelength band $\Lambda_{21}$, the intersection $\Lambda_1 = \Lambda_{11} \cap \Lambda_{21}$ can be used as the first wavelength band $\Lambda_1$. Similarly, when the detector arrangement 120 is arranged to detect a wavelength band $\Lambda_{12}$ and the pulse for the second wavelength band comprises photons from a wavelength band $\Lambda_{22}$, the intersection $\Lambda_2 = \Lambda_{12} \cap \Lambda_{22}$ can be used as the second wavelength band $\Lambda_2$. It is also noted that a pulse for the (initially determined) first wavelength band is also a pulse for the narrower (later determined) first wavelength band, wherein the narrower band takes the detector arrangement 120 into account in the aforementioned manner.

As will be discussed, the wavelength bands $\Lambda_1$ and $\Lambda_2$ are preferably optically separated e.g. with a beam splitter. The beam splitter may be arranged in the detector arrangement 120, and separates the aforementioned bands $\Lambda_1$ and $\Lambda_2$ from each other. When optically separated, the wavelength bands $\Lambda_1$ and $\Lambda_2$ do not overlap. In other words, the intersection of $\Lambda_1$ and $\Lambda_2$ is an empty set or comprises only one wavelength (an end point of $\Lambda_1$ and $\Lambda_2$). However, in principle the wavelength bands may overlap. In this case, however, the bands are not the same, i.e. the intersection of $\Lambda_1$ and $\Lambda_2$ is smaller than one of $\Lambda_1$ and $\Lambda_2$.

The method further comprises providing information 142 indicative of the intensity of the scattered light at the first wavelength band $\Lambda_1$ as function of time; and providing information 144 indicative of the intensity of the scattered light at the second wavelength band $\Lambda_2$ as function of time. For example the detector arrangement 120 may provide or be arranged to provide such information 142, 144 e.g. to the processing unit 130. The device further comprises means for providing the information 142, 144 from the detector arrangement 120 to the processing unit 130.

The method further comprises determining information indicative of the differential absorption between the two wavelengths bands using the measured intensities or the aforementioned information thereof. This information can be calculated e.g. by using the principles laid down in Eqns. 4 to 7 below. The information indicative of the differential absorption between the two wavelengths bands can be a product of the ratio of the intensities at a first relative time and the inverse ratio of the intensities at a second relative time (cf. Eq. 7).

Furthermore, the method comprises determining the temperature, pressure, and/or the molecular number density of the gaseous compound 910 as function of the distance d (FIG. 1*a*) from the location O in the first direction $D_1$ using the information indicative of the indicative of the differential absorption between the two wavelengths bands.

The corresponding device 100 comprises the processing unit 130 for determining (or arranged to determine) the temperature, pressure, and/or the molecular number density of the gaseous compound 910 as function of the distance d from the location O in the first direction $D_1$ using the measurement results of the detector 120; in particular by determining information indicative of the differential absorption between the two wavelengths bands using the information provided by the detector or the detectors.

In a preferred embodiment, the intensity of the backscattered light is measured as function of time and at (at least) the two wavelength bands, as depicted in FIG. 1*a*. In this embodiment, the pulse sequence is guided from the location O to the gaseous mixture 900 in a first direction $D_1$, whereby particles 920 of the gaseous mixture scatter back at least part of the light pulse(s) of the pulse sequence as a backscattered light to a second direction $-D_1$, wherein the second direction $-D_1$ is reverse to the first direction $D_1$. This embodiment comprises measuring, as function of time, the intensity of the backscattered light propagating in the second direction $-D_1$ at the first and the second wavelength bands $\Lambda_1$ and $\Lambda_2$.

In the corresponding device, the detector arrangement 120 is arranged to detect (i.e. measure) the intensity of the backscattered light.

Referring to FIG. 1*a*, the distance the light pulse 150 travels from the first location O before the scattering event (of FIG. 1*a*) is d. Moreover, the distance the scattered light pulse 160 travels before it becomes detected by the detector 120 is also d. Therefore, the time of flight of the light pulse 150, from the first location O to the detector 120 is $2d/c$, wherein c is the speed of light. In general, c depends on the gaseous mixture 900, but with good accuracy c is the speed of light in vacuum (i.e. about $3 \times 10^8$ m/s). Therefore, when the intensity of the scattered pulse 160 is detected at the time $t_1 = 2d/c$, one knows that the signal is the result of light that has propagated a distance $d = t_1 c/2$ from the location O into the thermal device.

Figure 1B:
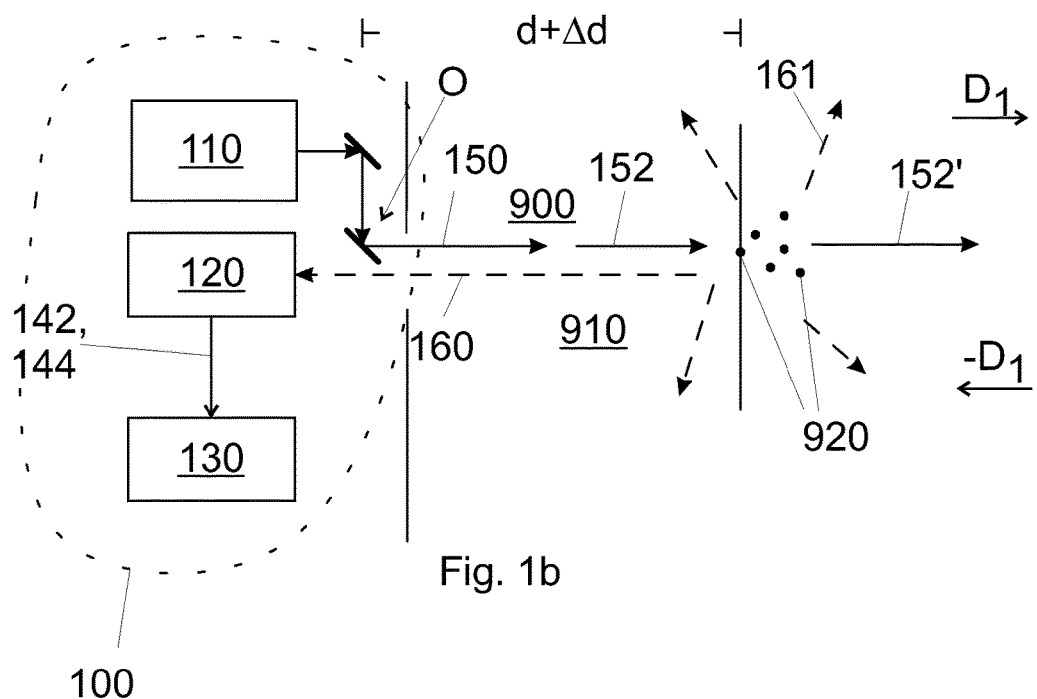
FIG. 1b shows a device and a method for measuring temperature, molecular number density, and/or pressure of a gaseous compound as function of distance at a second instance of time

As depicted in FIG. 1a, a part 152 of the light pulse travels without scattering at that time. Referring to FIG. 1b, this part becomes scattered later. In FIG. 1b, the part 152 becomes scattered after travelling an additional distance Δd; in addition to the distance d as discussed above. Therefore, when the intensity of the scattered pulse 160 is detected at the time $t_2=2(d+\Delta d)/c$, one knows that the signal is the result of light that has propagated a distance d+Δd. It is further noted, in particular the factor two, that $t_2-t_1=2\Delta d/c$. Also in this later scattering, a part 152' of the pulse 152 is not scattered. As is evident, multiple subsequent scattering occur from various particles. Typically the gaseous mixture 900 comprises particles almost everywhere, whereby the first observance of the scattered light pulse 160 bear evidence of the light pulse 150 entering the gaseous mixture 900.

Therefore, from the time one can deduce the distance the light pulse 150 has traveled. The components of the device 100 may provide for some additional delay. Typically the gaseous mixture 900 comprises particles almost everywhere, whereby the first observance of the scattered light pulse 160 bears evidence of the light pulse 150 entering the gaseous mixture 900.

It is noted that the event of multiple scattering (back and forth) is excluded from the analysis. As scattering attenuates the signal, multiple scattering makes the intensity of the respective multiply scattered signal negligible low.

Figure 1C:
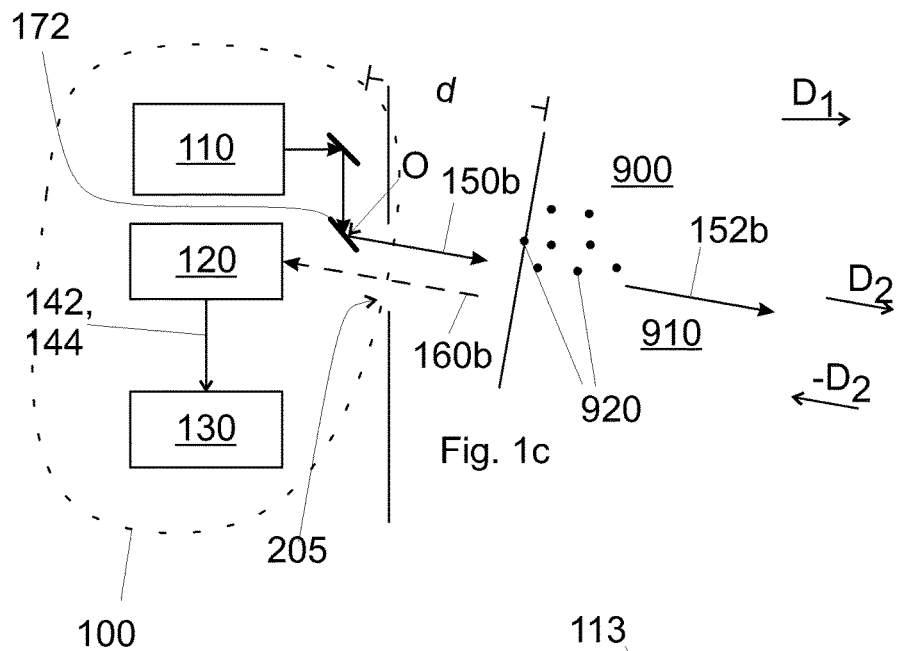
FIG. 1c shows a device and a method for measuring temperature, compound as function of distance, after changing the direction to which a light pulse is guided.
Figure 2A:
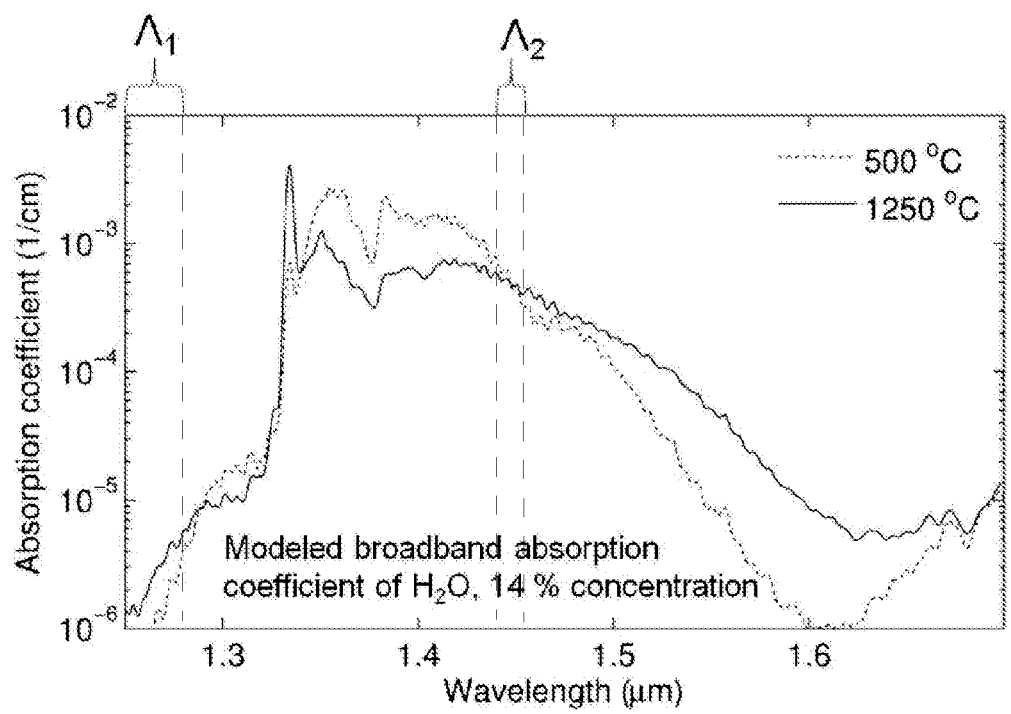
FIG. 2a shows the selection of a first wavelength band and a second wavelength band for the measurement of molecular number density.
Figure 2B:
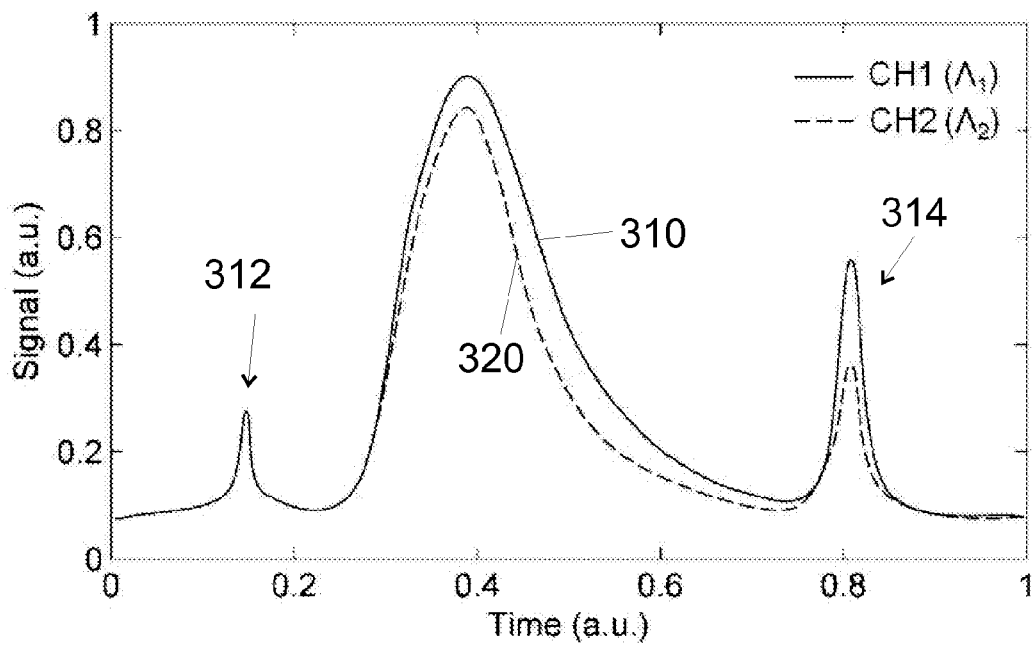
FIG. 2b shows two measured signals, of which one corresponds to the first wavelength band and the other corresponds to the second wavelength band.

FIG. 2b shows an example of the intensity 310 of the scattered light pulse 160 at a first wavelength band $\Lambda_1$ as function of time t, as measured by a detector arrangement 120. The optical power and the intensity are related via the area of a detector. FIG. 2b also shows an example of the intensity 320 of the scattered light (i.e. a scattered light pulse 160) at a second wavelength band $\Lambda_2$ as function of time t. The reference CH1 refers to a first channel of the detector arrangement 120, and the reference CH2 refers to a second channel of the detector arrangement 120. The first channel CH1 of the detector arrangement 120 is arranged to detect the intensity 210 of the scattered light at the first wavelength band $\Lambda_1$. The second channel CH2 of the detector arrangement 120 is arranged to detect the intensity 210 of the scattered light at the second wavelength band $\Lambda_2$. The peak 312 is a result of the light pulse scattering from the optics, e.g. the mirror 172 (FIG. 1c) at the location O. The peak 314 is a result of light scattering (or reflecting) from a wall (not shown) of the thermal device. As the interior of the thermal device is closed, a scattering (or reflecting) wall is located somewhere in the direction of D1, cf. FIG. 1a. In between, the decreasing intensity is due to absorption to gas molecules. The increasing part is due to collection optics, which focus the pulse 150 to a location in between the location O and the scattering wall. As shown in the figure (and also in FIG. 3b) the signals decrease in a different way, which provides information indicative of the differential absorption between the two wavelength bands, which information can be used to determine the temperature, the molecular number density, and/or the pressure.

A typical thermal device comprises a member 204 having an inlet, and another wall, or another region of the same wall located opposite the optical inlet 205 in such a way that the scape is left in between the optical inlet and the other wall or the other region. In a typical thermal device the distance between the optical inlet 205 and the opposite region, i.e. the linear size of the space, is at most 50 m or at most 20 m. In a typical thermal device the distance between the optical inlet 205 and the opposite region, i.e. the linear size of the space, is at least 2 m or at least 5 m. The linear size may thus be from 2 m to 50 m, such as from 5 m to 20 m. This has implications on spatial accuracy required from the method. For example, the spatial accuracy of the method may be selected such, that the profile becomes detected in at least 10 points between the aforementioned linear size.

The selection of the first and the second wavelength bands $\Lambda_1$ and $\Lambda_2$ (and optionally other bands) depends on what (which gaseous compound or compounds, and which quantity or quantities) is to be measured from the gaseous mixture 900 using the pulse sequence.

The case, where the molecular number density is measured, will be discussed first with reference to FIG. 2a. In this case, the method comprises selecting the first wavelength band $\Lambda_1$ such that the total attenuation factor for the light pulse 150, the first wavelength band $\Lambda_1$, and the gaseous compound 910 has a first value $\kappa_{tot1}$, selecting the second wavelength band $\Lambda_2$ such that the total attenuation factor for the light pulse 150, the second wavelength band $\Lambda_2$, and the gaseous compound 910 has a second value $\kappa_{tot2}$, the first value $\kappa_{tot1}$ is different from the second value $\kappa_{tot2}$, and determining the molecular number density of the gaseous compound as function of the distance from the location in the first direction.

The total attenuation factor depends on the absorption cross section of the gaseous compound and the wavelength band of the pulse source in a way to be defined later.

The ratio of the greater of $\kappa_{tot2}$ and $\kappa_{tot1}$ to the smaller of $\kappa_{tot2}$ and $\kappa_{tot1}$ may be e.g. at least 10, at least 100, or at least 1000; or even more. It may also be undefined, provided that the smaller of $\kappa_{tot2}$ and $\kappa_{tot1}$ equals zero (i.e. no absorption occurs due the gaseous compound 910 for the wavelength or wavelengths of the wavelength band; even if absorption to other gaseous compounds of the mixture 900 may occur). It may also be hard to calculate, when the smaller of $\kappa_{tot2}$ and $\kappa_{tot1}$ is close to zero, such as less than $10^{-23}$ cm$^2$, less than $10^{-24}$ cm$^2$ or less than $10^{-25}$ cm$^2$. The wavelength bands may be selected in the prescribed way in case a supercontinuum is used as the light pulse; or in the case the light pulse source one or more conventional pulse lasers. Moreover, in the more general case, wherein multiple wavelength bands are used, the ratio of the greatest total attenuation factor (for a gaseous compound) to the smallest total attenuation factor (for the same gaseous compound), at a temperature, may be e.g. at least 2, at least 5, at least 10, at least 100, or at least 1000; or even more. It may also be undefined or hard to calculate, provided that the smallest total attenuation factor equals zero or is close to zero (as discussed above). These total attenuation factors depend on temperature, as the absorption cross section depends on temperature.

As is clear for a person skilled in the art, in case conventional pulse lasers are used to generate the light pulse 150, the first value $\kappa_{tot1}$ of the total attenuation factor corresponds to the absorption coefficient of the gaseous compound at the wavelength of a first laser. In this case, the second value $\kappa_{tot2}$ of the total attenuation factor corresponds to the absorption coefficient of the gaseous compound at the wavelength of a second laser.

In case two conventional lasers are used, their pulses may be optically combined to a single pulse, of which spectrum comprises two well defined peaks. However, it is also possible to not combine the pulses. A first pulse for the first wavelength band $\Lambda_1$ may be generated first, and the corresponding intensity of the scattered pulse measured. Subsequently, another pulse for the second wavelength band $\Lambda_2$ may be generated, and the corresponding intensity of the scattered other pulse measured. These subsequent pulse are referred to as pulse sequence, and the scattered pulses are referred to as scattered light.

In case a supercontinuum light pulse source, the first value $\kappa_{tot1}$ of the total attenuation factor is a measure of the absorption coefficient over the first wavelength band, wherein the absorption coefficient $\alpha$ is a product of absorption cross section $\sigma$ and molecular number density $N/V$. For example, if the intensity spectrum of the supercontinuum laser pulse 150 is $I_0(\lambda)$, the total intensity over the first wavelength band is $$I_0 = \int_{\Lambda_1} I_0(\lambda) d\lambda. \quad (1)$$

However, the gaseous compound attenuates (absorbs and scatters) the pulse 150 and the scattered pulse 160, and the backscattering itself may attenuate the backscattered pulse. Moreover, depending on how collimated the light pulse and/or the scattered light pulse 160 is, the intensity may decrease as function of distance. In what follows it is assumed that the light pulse 150 is collimated, while the scattered pulse 160 is not collimated. Therefore, after the collimated light pulse 150 has travelled the distance d; scattered to the scattered pulse 160, possibly thereby attenuated by a backscattering coefficient $\beta$, and the scattered (uncollimated) light pulse travelled the distance d; the intensity is at the detector 120 is $$I(\lambda) = \frac{\beta(\lambda)}{d^2} I_0(\lambda) \exp(-\alpha(\lambda) 2d) = \frac{\beta(\lambda)}{d^2} I_0(\lambda) \exp\left(-\sigma(\lambda) \frac{N}{V} 2d\right), \quad (2)$$

wherein $I_0(\lambda)$ is the spectrum of the light pulse 150 when emitted by the light pulse source, d is the distance (cf. FIG. 1; the factor 2 comes from the light pulse 150 and the scattered light pulse 160 travelling the distance d), $\alpha(\lambda)$ is the wavelength dependent absorption coefficient, $\sigma(\lambda)$ is the wavelength dependent absorption cross section, $N/V$ the molecular number density, and $\beta(\lambda)$ the backscattering coefficient, defining the amount of light backscattered. In general, due to the scattering in multiple directions, the intensity of scattered light decreases as $d^2$. Note that here only $d^2$ is used, instead of $(2d)^2$, since only the scattered light propagates to multiple directions, while the light pulse 150 is collimated. The scattering coefficient may be independent of the wavelength. In general, the molecular number density $N/V$ and/or the absorption coefficient $\sigma(\lambda)$ may depend on the location d, whereby an integral should be used instead of the simpler produce; however for the definition of the total attenuation factors $\kappa_{tot1}$ and $\kappa_{tot2}$ these approximations can be made.

The first total attenuation factor $\kappa_{tot1}$ is defined as a constant, such that when used instead of the absorption coefficient in the Beer-Lambert law, the total attenuation factor gives the same total intensity at the first wavelength band $\Lambda_1$. I.e.

$$I = \int_{\Lambda_1} I(\lambda) d\lambda = \int_{\Lambda_1} \frac{\beta(\lambda)}{d^2} I_0(\lambda) \exp\left(-\sigma(\lambda) \frac{N}{V} 2d\right) d\lambda = \quad (3)$$

$$\int_{\Lambda_1} \frac{\beta(\lambda)}{d^2} I_0(\lambda) \exp\left(-\kappa_{tot1} \frac{N}{V} 2d\right) d\lambda.$$

As for the temperature, the absorption coefficient $\sigma(\lambda)$ may depend, and generally does depend at least for some wavelengths, on the temperature. Therefore, the total attenuation factor $\kappa_{tot1}$ (and $\kappa_{tot2}$ and $\kappa_{tot3}$ in a corresponding way) is dependent on temperature. The second total attenuation factor $\kappa_{tot2}$ can be defined similarly; the computation performed over the range $\Lambda_2$. As is clear from the equation, the total attenuation factors $\kappa_{tot}$ depend on the spectrum of the light pulse 150 and the spectrum of the absorption coefficient $\sigma(\lambda)$.

For measuring the molecular number density, and referring to FIG. 2a, the first wavelength band $\Lambda_1$, can be selected such that the total attenuation factor $\kappa_{tot1}$ of light of the first wavelength band, to the gaseous compound 910, is low. FIG. 2a shows the absorption coefficient $\alpha(\lambda)$, when the gaseous compound 910 is steam, and for the concentration 14%. Absorption coefficient is shown for the temperatures 500° C. and 1250° C. As will be discussed, the concentration x depends on the molecular density $N/V$. At the temperature 500° C. and the pressure 1 atm, this concentration corresponds to the molecular density $1.3 \times 10^{24}/m^3$; and at the temperature 1250° C. and the pressure 1 atm, this concentration corresponds to the molecular density $7 \times 10^{23}/m^3$. For example, in the case of FIG. 2a, the first wavelength band may be from 1.25 μm to 1.27 μm. As shown in FIG. 2a, the absorption coefficient for these wavelengths is small, whereby the total attenuation factor $\kappa_{tot1}$ is small.

Referring to FIG. 2a, the second wavelength band $\Lambda_2$ can be selected such that total attenuation factor $\kappa_{tot2}$ of light of the second wavelength band, to the gaseous compound 910, is higher than the first total attenuation factor $\kappa_{tot1}$. For example, in the case of FIG. 2a, the second wavelength band may be from 1.44 μm to 1.46 μm. As shown in FIG. 2a, the absorption coefficient for these wavelengths is considerably larger than for the longer wavelengths; larger by three orders of magnitude.

FIG. 2a is an to be used only as an example, but applies as such, when the molecular number density of water is measured.

As molecular number density is to be measured, the second band $\Lambda_2$ can be selected also in such a way that the larger of the total attenuation factors ($\kappa_{tot2}$ in the present case) is independent or essentially independent on temperature, as shown in FIG. 2a. The term "essentially independent" refers to a relative dependence of less than 1%/100 K, i.e. less than 100 ppm/K (ppm for parts per million, i.e. $10^{-6}$). A corresponding embodiment of the method comprises selecting the first or the second wavelength band ($\Lambda_1$, $\Lambda_2$) such that the temperature dependence of the first or the second total attenuation factor ($\kappa_{tot1}$, $\kappa_{tot2}$) is less than 100 ppm/K. In a preferred embodiment, the larger of the attenuation factors has this small temperature dependence. Therefore, when measuring the molecular number density, the attenuation factors $\kappa_{tot1}$, $\kappa_{tot2}$ can be assumed known irrespective of the temperature profile of the gaseous compound 910.

In FIGS. 2a, 2b, 3a, and 3b, a supercontinuum laser is used as the light pulse source.

In the present method, when molecular density $N/V$ is measured and only two wavelength bands are used such that the total attenuation factors are independent of temperature, the temperature needs not to be known. For other selection of wavelength bands, even if such a selection is not preferred, a known temperature profile may be assumed.

In the present method, when the concentration x, having the unit ppm (or similar), which is determinable from the molecular density $N/V$ by $x=(N/V) \times (kT/p)$, wherein k is the Boltzmann constant, T the temperature and p the pressure, is to be measured, the temperature and the pressure need to be measured or assumed known. Moreover, one of them can be measured, while the other can be assumed known. E.g. the molecular density N/V and the temperature T profiles can be measured as will be discussed, while the pressure may be assumed constant and known. It may be known to be atmospheric, or it may be measured with another device.

In the present method, one may assume that light at the first wavelength band scatters from particles and gas molecules in a similar way that light at the second wavelength band. In this way, one channel provides a reference for the other channel. In the case mentioned above, since the molecules do not significantly absorb light at the first band, the first band provides a reference for the second band. It is also noted that other gas compound(s) may absorb light, and it is assumed that this absorption is similar for both the wavelengths bands. It has been observed, that even if the scattering coefficient β has some wavelength dependence, this typically averages out of the equation, when a light pulse having a wide spectrum is used. This happens e.g. with the supercontinuum light pulse source.

Denoting the signal of the channel CH1 as $S_1(t)$, one may write for the decrement of the signal; using the Beer-Lambert law:

$$S_1(t + \Delta t) = S_1(t) e^{-\left[\frac{N(d(t))}{V} \kappa_{tot1} 2\Delta d\right]}. \quad (4)$$

Here d(t) is the distance the light pulse has travelled, i.e. d=tc/2, as discussed above, and Δd is the distance the light of the pulses 150 and 160 travel during the time interval Δt; whereby Δt=2Δd/c, as discussed above. $\kappa_{tot1}$, is the total attenuation factor for light having the wavelength of the first wavelength band $\Lambda_1$, as discussed and defined above. The factor 2 in the exponent comes from the fact that both the light pulse 150 and the scattered light pulse 160 travel the distance Δd during the time Δt. N(d(t))/V is the molecular number density of interest at the distance d(t) in the direction $D_1$ from the location O.

Denoting the signal of the channel CH2 as $S_2(t)$, one may write for the decrement of the signal; using the Beer-Lambert law:

$$S_2(t + \Delta t) = S_2(t) e^{-\left[\frac{N(d(t))}{V} \kappa_{tot2} 2\Delta d\right]}. \quad (5)$$

Here $\kappa_{tot2}$ is the total attenuation factor for light having the wavelength of the second wavelength band $\Lambda_2$. The second total attenuation factor $\kappa_{tot2}$ was discussed and implicitly defined above.

Dividing Eq. 5 by Eq. 4 and taking logarithm gives $$\frac{N(d(t))}{V} 2\Delta d(\kappa_{tot1} - \kappa_{tot2}) = \ln\left[\frac{S_1(t)S_2(t + \Delta t)}{S_2(t)S_1(t + \Delta t)}\right], \quad (6)$$

from which the molecular number density as function of location, i.e. N(d(t))/V can be calculated, since the signals $S_1$ and $S_2$ are measured as function of time t. The location d(t), on the other hand is a function of time t, as discussed above. Inserting Δd=(cΔt)/2, and solving for the molecular number density gives $$\frac{N(d(t))}{V} = \frac{1}{c\Delta t(\kappa_{tot1} - \kappa_{tot2})} \ln\left[\frac{S_1(t)S_2(t + \Delta t)}{S_2(t)S_1(t + \Delta t)}\right]. \quad (7)$$

It is noted that here the property "molecular number density" has the unit of atoms per volume, such as $1/m^3$. If the unit $mol/m^3$ is to be used, the division with Avogadro's number is needed. Thus, in order to obtain a proportional concentration, such as mol-% or vol-%, the total number of atoms and molecules needs to be known. This may be solved from the gas equation $p=(N_t/V)kT$; wherein p is pressure, $N_t$ the total number of atoms and molecules of the gases of the gaseous mixture, V is the volume, k is the Boltzmann constant, and T is the temperature. In other words, $N_t/V$ is the gas content in 1/V. Thus, the molecular concentration $N/N_t$ would be simply the calculated molecular number density (N/V) divided by $N_t/V$.

It is furthermore noted, that in case the signals $S_1$ is a result of a pulse, and $S_2$ is a result of another, subsequent pulse, instead of absolute time, relative time should be used in Eqns. 6 and 7. The term relative time means that the relative time is set to zero when the corresponding pulse has a predetermined location; wherein the location is the same for all the pulses of the pulse sequence. For example, the time may be set zero always at the generation of the pulse. For example, the time may be set zero always when the pulse enters the space comprising the gaseous mixture.

In the above, the time difference Δt between two instances of time may equal the time difference between two subsequent samples, rising from the sampling rate of the detector 120 and/or the processing unit 130; or Δt may be an integer multiple thereof. In what follows, Δt is used to denote the time difference between two subsequent samples.

Figure 3A:
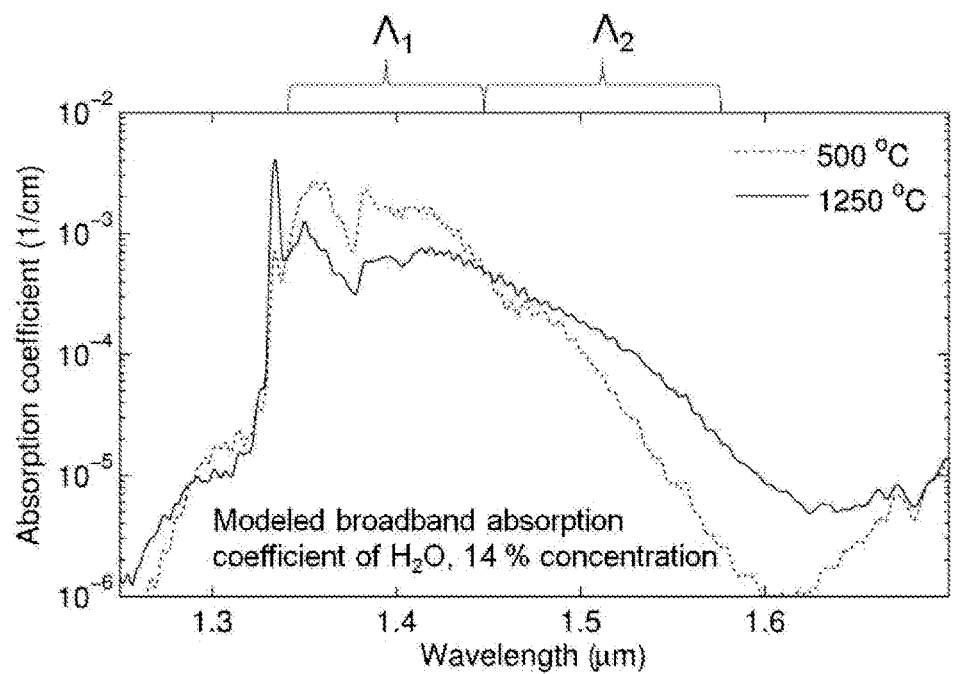
FIG. 3a shows the selection of a first wavelength band and a second wavelength band for the measurement of temperature.
Figure 3B:
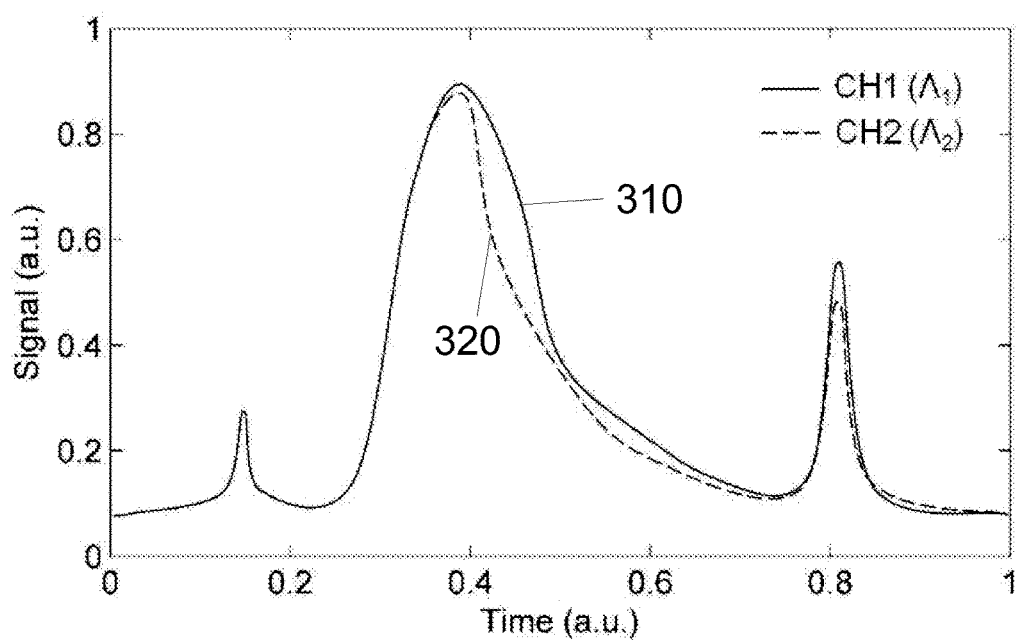
FIG. 3b shows two measured signals, of which one corresponds to the first wavelength band and the other corresponds to the second wavelength band.

As for measuring the temperature, FIGS. 3a and 3b show the selection of the first wavelength band $\Lambda_1$ (and the corresponding first channel CH1) and the second wavelength band $\Lambda_2$ (and the corresponding second channel CH2) in the case, where the temperature is measured. In this case, the method comprises selecting the first wavelength band $\Lambda_1$ such that the total attenuation factor $\kappa_{tot1}$ for the light pulse 150, the first wavelength band $\Lambda_t$, and the gaseous compound 910 depends on temperature in a first way, selecting the second wavelength band $\Lambda_2$ such that the total attenuation factor $\kappa_{tot2}$ for the light pulse 150, the second wavelength band $\Lambda_2$, and the gaseous compound 910 depends on temperature in a second way, the first way is different from the second way, and determining the temperature of the gaseous compound 910 as function of the distance from the location in the first direction.

FIG. 3a shows the spectrum of the absorption coefficient of $H_2O$ at two temperatures $T_1=500°$ C. and $T_2=1250°$ C., for the concentration 14%, (for the corresponding molecular densities, c.f. discussion in connection with FIG. 2a). Referring to FIG. 3a, the first wavelength band $\Lambda_1$ can be selected in such a way that the first total attenuation factor $\kappa_{tot1}$ depends on temperature in a first way; in FIG. 3a, the first total attenuation factor decreases as temperature increases. Referring to FIG. 3a, the second wavelength band $\Lambda_2$ can be selected in such a way that the second total attenuation factor $\kappa_{tot2}$ depends on temperature in a second way; in FIG. 3a, the second total attenuation factor increases as temperature increases. In this case, the product of partial temperature derivate of $\kappa_{tot2}$ and the partial temperature derivate of $\kappa_{tot1}$ is be negative.

Other possibilities include one wherein the first wavelength band $\Lambda_1$ is selected in such a way that first total attenuation factor $\kappa_{tot1}$ is independent or essentially independent of temperature. The second wavelength band $\Lambda_2$ can be selected in such a way that the second total attenuation factor $\kappa_{tot2}$ depends on temperature. The term essentially independent can here be defined to mean that the maximum total attenuation factor differs from the minimum total attenuation factor by at most 10%, or at most 50% in the temperature range from 300° C. to 1000° C. As for the concepts "minimum" and "maximum" above, it is noted that the attenuation factor can be considered to be a function of temperature, whereby the maximum correspond to a temperature and the minimum corresponds to another temperature. Correspondingly, when the second the total attenuation factor $\kappa_{tot2}$ depends on temperature, the maximum total attenuation can differ from the minimum total attenuation factor by at least 50%, or at least 100% in the temperature range from 300° C. to 1000° C.

Moreover the bands $\Lambda_1$ and $\kappa_2$ can be selected in such a way that both total attenuation factors $\kappa_{tot1}$ and $\kappa_{tot2}$ e.g. increase with increasing temperature, but either $\kappa_{tot1}$ or $\kappa_{tot2}$ increases more rapidly than the other. For example, the partial temperature derivate of $\kappa_{tot2}$ may be at least 10%, at least 50% or at least 100% more than the partial temperature derivate of $\kappa_{tot1}$. For example both attenuation factors and may decrease with increasing temperature, but either $\kappa_{tot1}$ or $\kappa_{tot2}$ can decrease more rapidly than the other. For example, the partial temperature derivate of $\kappa_{tot2}$ may be at least 10%, at least 50% or at least 100% more than the partial temperature derivate of $\kappa_{tot1}$ (note, that since the total attenuation factors in the last case are negative, the latter expression "more" refers to a more negative value).

When the total attenuation factors depend on temperature in different ways, at some temperature, the values of the total attenuation factors are also different. Therefore, at a temperature, the ratio of the greatest total attenuation factor (for a gaseous compound) to the smallest total attenuation factor (for the same gaseous compound) may be e.g. at least 2, preferably at least 4; or even more as discussed above. It may also be undefined or hard to calculate, provided that the smallest total attenuation factor equals zero or is close to zero in the sense discussed above.

As for measuring the temperature profile, when only two wavelength bands are used, the molecular number density profile on the optical path of the light pulse is assumed known. The molecular number density profile may be assumed e.g. constant.

As for the calculation of the temperature, the calculations proceed in a similar manner that was already discussed for the molecular number density. By dividing Eg. (5) with Eq. (4), one may obtain the equation for $[N(d)(\kappa_{tot1}-\kappa_{tot2})]/V$. When the molecular number density N/V can be considered to be known, e.g. constant, the difference of the attenuation factors, i.e. $\kappa_{tot1}-\kappa_{tot2}$, can be solved from this equation. Since the dependencies of the attenuation factors on the temperature is known, temperature can be solved.

In some embodiments, a wavelength band is selected in such a way that reasonable molecular absorption is expected to occur to the gas molecules of the gaseous compound 910. As an example, a wavelength band may be selected such that the expected molecular absorption is at least 1%. This is to ensure reasonable absorption in at least wavelength band. Optionally, for this band, the expected molecular absorption may be at most 99%. The term expected molecular absorption is herein defined as follows. When selecting the wavelength band, a concentration x for the gaseous compound can be expected, e.g. a minimum detectable concentration. Moreover, the length of L the optical path of the light pulse 150 is known, such as a length of a gas duct. By the Beer-Lambert law (cf. Eq. 2), the expected molecular absorptance, i.e. the molecular absorptance that is expected in these conditions, is $$\frac{I_0 - I}{I_0} = \frac{\int_{\Lambda_i} I_0(\lambda) - I_0(\lambda)\exp\left(-\sigma(\lambda)\frac{N}{V}2L\right)d\lambda}{\int_{\Lambda_i} I_0(\lambda)d\lambda}, \qquad (8)$$

where $(N/V)=x\times(p/kT)$ is the molecular density as discussed above, and $\Lambda_i$ is the wavelength band to be chosen; it may be the first, the second, the third, or another wavelength band. In case $I_0(\lambda)$ and $\sigma(\lambda)$ are reasonably constant in terms of the wavelength, the formula for expected molecular absorptance reduces to $1-\exp(-2\sigma xpL/kT)$, wherein $\sigma$ is the absorption cross section (available from tables), x is the design concentration, p is the design pressure, L is the design length, k is the Boltzmann constant, and T is the design temperature (in Kelvin). The term "design" here refers to the environment, wherein the method is designed to work. In a similar way, the (actual) molecular absorptance is calculated by Eq. 8, when the actual pressure, length, concentration, and temperature are known.

As an example, for a constant gas concentration of about 14% and pressure 1 atm, and an absorption cross section of $1.2\times10^{-21}$ cm$^2$ at 500° C., a 20 m long path (i.e. a 10 m wide channel propagated back and forth) results in 96% molecular absorptance, and in case these are the design conditions, also in 96% expected molecular absorptance. In a similar way, the expected molecular absorptance for other wavelength bands $\Lambda_2, \Lambda_3, \Lambda_4, \ldots$ is defined by Eq. 8 and using the design values of p, L, and T. In a similar way, the molecular absorptance for other wavelength bands $\Lambda_2, \Lambda_3, \Lambda_4, \ldots$ is defined by Eq. 8 using the actual values of p, L, and T.

An embodiment comprises selecting a wavelength band such that the molecular absorptance or expected molecular absorptance for the wavelength band is at least 1%. The embodiment may further comprise selecting the wavelength band (e.g. the first or the second band) such that the expected molecular absorptance or the molecular absorptance for the wavelength band at most 99%; or from 2% to 99%; or from 2% to 97%.

This value provides for reasonable absorptance for measurements. These selection criterion may apply also for at least a further wavelength band. However, one channel may serve as a reference, whereby no molecular absorptance is needed in that channel. The corresponding embodiment may further comprise selecting a wavelength band (e.g. the first or the second band) such that the expected molecular absorptance or the molecular absorptance for at least one wavelength band is from 0% to 99%; or from 1% to 99%; or from 2% to 99%; or from 2% to 97%. An embodiment comprises selecting the wavelength bands such that at least one of molecular absorptances or expected molecular absorptances for the wavelength bands is at least 1%, and another of the molecular absorptances or expected molecular absorptances for the wavelength bands is at most 99%. Preferably all the molecular absorptances or expected molecular absorptances for the wavelength bands are from 0% to 99%; while at least one of the molecular absorptances or the expected molecular absorptances for a wavelength band is from 1% to 100% and optionally at most 99%; or from 2% to 99% or from 2% to 97%.

A typical device may be arranged to detect changes in intensities, wherein the changes are at least 0.1%. For the aforementioned case, a temperatures dependence of the absorption cross section should be at least 0.07% per Kelvin in order for a 50° C. temperature change to cause a 0.1% change in the ratio of intensities at the temperature of about 500° C. In a higher temperature, such as 1200° C., 0.013% per Kelvin should be sufficient for detecting a 50° C. temperature change. This applies for a narrow band, such as ordinary laser, and also for a wide band through the total attenuation factor(s) $\kappa_{tot}$ defined above. In an embodiment, a wavelength band ($\Lambda_1$ or $\Lambda_2$) and a wavelength source are selected such that the corresponding total attenuation factor ($\kappa_{tot1}$ or $\kappa_{tot2}$, respectively) has an absolute temperature dependence of at least 0.01% per Kelvin (100 ppm/K). The term absolute temperature dependence refers to an absolute value of the temperature dependence, e.g. temperature dependence may be at least 100 ppm/K or at most −100 ppm/K. Preferably this absolute temperature dependence is at least 0.02% per Kelvin (200 ppm/K). An embodiment comprises selecting the first and the second wavelength band ($\Lambda_1$ and $\Lambda_2$) such that the absolute temperature dependence of the first total attenuation factor $\kappa_{tot1}$ is less than 100 ppm/K and the absolute temperature dependence of the second total attenuation factor $\kappa_{tot2}$ is at least 100 ppm/K.

In general, more wavelength bands can be used for various purposes, as will be discussed. In general, in an embodiment at least one total attenuation factor (e.g. the first) has an absolute temperature dependence of at least 100 ppm/K and at least another total attenuation factor (e.g. the second) depends on the temperature in a different way than the one total attenuation factor (e.g. the first).

Figure 3C:
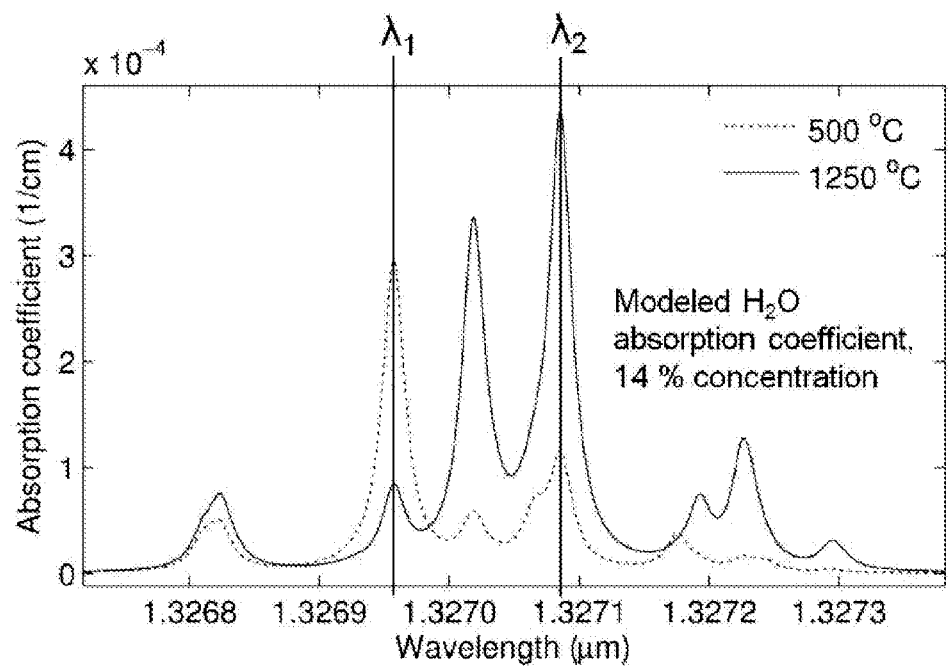
FIG. 3c shows the selection of a first wavelength (i.e. a narrow wavelength band) and a second wavelength (i.e. a narrow wavelength band) for the measurement of temperature.

FIG. 3c shows and example for measuring temperature with two very narrow bands $\Lambda_1$ and $\Lambda_2$, such as by using two conventional lasers. Also in FIG. 3c the first wavelength $\lambda_1$, i.e. the narrow wavelength band $\Lambda_1$, is selected in such a way that the first total attenuation factor $\kappa_{tot1}$ decreases as temperature increases. Referring to FIG. 3c, the second wavelength $\lambda_2$, i.e. the narrow second wavelength band $\Lambda_2$, is selected in such a way that the second total attenuation factor $\kappa_{tot2}$ increases as temperature increases.

As for calculation of pressure, it is known that pressure widens the absorption peaks of gases. However, in general, the integral of the peak remains substantially constant in the widening. Because of these issues, pressure affects the absorption cross section for a narrow wavelength band, wherein the width of the band is smaller than the width of the spectral peak of the gas compound. Thus, pressure is measurable in the same way as temperature, provided that a light pulse source producing light at only a narrow wavelength band is used. From the Eq. (6) the aforementioned quantity can be solved, wherefrom a difference in the absorption cross spectrum for a specific wavelength can be measured. Provided that temperature and molecular number density are constant, the pressure can be solved, when the form of the absorption spectrum as function of pressure is known. E.g. a conventional laser may suffice for one of the bands $\Lambda_1$ and $\Lambda_2$. It is noted that for the other band a light source with wider output spectrum can be used.

The partial pressure of the gaseous compound can also be calculated from the measured molecular density (N/V) and temperature T, since the partial pressure is p=(N/V)kT. The molecular density (N/V) and temperature T can be measured subsequently in a way that has been discussed, or simultaneously, as will be discussed later.

Figure 4:
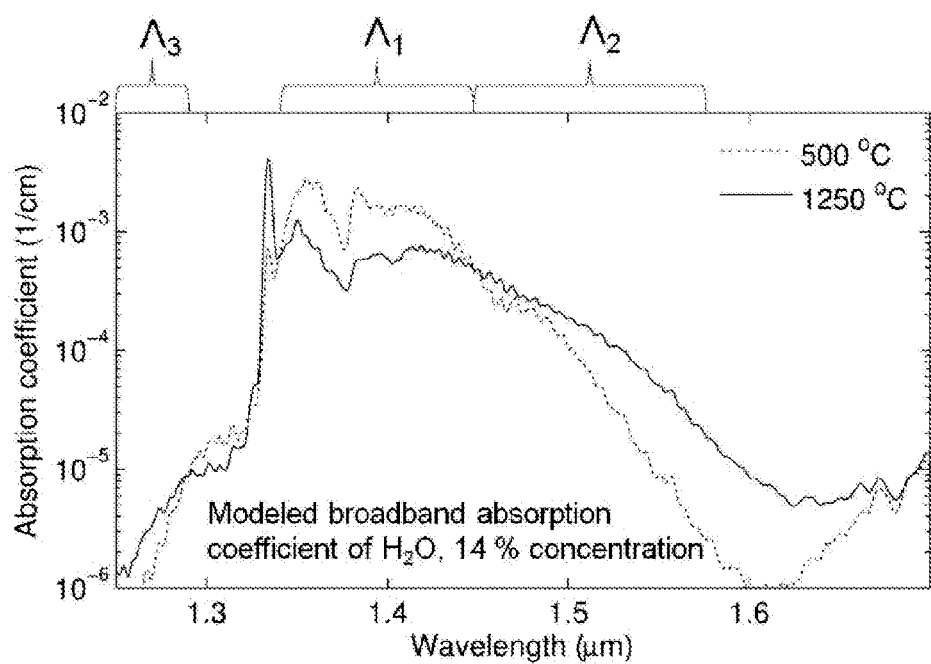
FIG. 4 shows the selection of a first wavelength band, a second wavelength band, and a third wavelength band for the measurement of temperature and molecular number density.

FIGS. 2a, 3a, and 4 show the absorption coefficient α as function of wavelength for stream ($H_2O$) at two different temperatures and in the conditions given above. Other interesting gaseous compounds 910 include $CO_2$ (carbon dioxide), $O_2$ (oxygen), CO (carbon monoxide), $NH_3$ (ammonia), $NO_X$ (compounds of nitrogen and oxygen, such as NO, $NO_2$, $N_2O$, $N_4O$, $NO_3$, $N_2O_3$, $N_2O_4$, $N_2O_5$, $N(NO_2)_3$) and $SO_X$ (compounds of sulphur and oxygen such as SO, $SO_2$, $SO_3$, $S_2O_2$, $S_6O_2$, $S_2O_2$). Therefore in some embodiments of the method the gaseous compound 910 comprises at least one of $H_2O$, $O_2$, $CO_2$, CO, $NH_3$, $NO_X$, and $SO_X$; and the method comprises selecting the first wavelength band $\Lambda_1$ and the second wavelength band $\Lambda_2$ using information on the spectrum the absorption cross section σ and/or information on the temperature dependence of the absorption cross section σ of the gaseous compound 910 that the gaseous mixture 900 comprises.

Preferably the gaseous compound 910 comprises at least one of $H_2O$ and $CO_2$. These gases have been noticed to have spectral properties particularly suitable for the measurement of temperature, molecular number density, and/or pressure.

However, the gaseous mixture 920 may comprise, in addition to the gaseous compound 910 also other gaseous compounds. These other gaseous compounds have a wavelength-dependents absorption cross section, which may also be dependent on temperature. These other gaseous compounds may also include at least one of $H_2O$, $O_2$, $CO_2$, CO, $NH_3$, $NO_X$, and $SO_X$. As for the method for the determination of the molecular number density, an embodiment of the method comprises selecting the first wavelength band such that the first total attenuation factor for the light pulse, the first wavelength band $\Lambda_1$, and the gaseous compound 910 has a first value $\kappa_{tot1}$. When the possibility of the presence of the other gaseous compounds is considered, this selection may be done in such a way that the first total attenuation factor for the light pulse, the first wavelength band, and the other gaseous compound has a value $\kappa_{tot1,other}$ that is negligible small in respect to the first value of the total attenuation factor. The value $\kappa_{tot1,other}$ is calculated as $\kappa_{tot1}$ (cf. Eq. 3), however using the spectrum of absorption cross section of the other gaseous compound. Negligible small may refer to the ratios $\kappa_{tot1,other}/\kappa_{tot1}$ of at most 50%, at most 25%, or at most 1%. However, the first wavelength band $\Lambda_1$ and the second wavelength band $\kappa_2$ may be selected also such that both the total attenuation factors $\kappa_{tot1,other}$ and $\kappa_{tot1}$ are small in comparison to the second total attenuation factor $\kappa_{tot2}$. In this case, the ratio $\kappa_{tot1,other}/\max(\kappa_{tot1}, \kappa_{tot2})$ may be e.g. at most 10%, at most 5%, or at most 1%. Moreover, in this case, the selection of the second wavelength band $\Lambda_2$ may be done in such a way that the total attenuation factor for the light pulse, the second wavelength band, and the other gaseous compound has a value $\kappa_{tot2,other}$ that is negligible small in respect to the first or the second value of the attenuation factor, i.e. the ratio $\kappa_{tot2,other}/\max(\kappa_{tot1}, \kappa_{tot2})$ may be e.g. at most 10%, at most 5%, or at most 1%.

As for the determination of the temperature, the wavelength bands can be selected in such a way that the other or both of the other total attenuation factors is small, i.e. $\kappa_{tot1,other}/\max(\kappa_{tot1}, \kappa_{tot2})$ and/or $\kappa_{tot2,other}/\max(\kappa_{tot1}, \kappa_{tot2})$ may be e.g. at most 10%, at most 5%, or at most 1%.

For measuring at least two of temperature, molecular number density and pressure, a third wavelength band is selected, as will be discussed. This selection gives rise to a third attenuation factor $\kappa_{tot3}$, i.e. the attenuation factor for the light pulse, the third wavelength band $\Lambda_3$, and the gaseous compound; and to a third other attenuation factor $\kappa_{tot3,other}$, i.e. the attenuation factor for the light pulse, the third wavelength band $\Lambda_3$, and the other gaseous compound. The wavelength bands can be selected such that at least one or some of the other attenuation factors is/are small. More specifically: $\kappa_{tot1,other}/\max(\kappa_{tot1}, \kappa_{tot2}, \kappa_{tot3})$ and/or $\kappa_{tot2,other}/\max(\kappa_{tot1}, \kappa_{tot2}, \kappa_{tot3})$ and/or $\kappa_{tot3,other}/\max(\kappa_{tot1}, \kappa_{tot2}, \kappa_{tot3})$ may be e.g. at most 10%, at most 5%, or at most 1%.

The information on the spectrum the absorption cross section is available from the literature on optical spectroscopy. Moreover, the information on the temperature dependence of the absorption cross section is available from the literature on optical spectroscopy. As discussed above, the total absorption coefficient $\kappa_{tot1}$ is a result of (i) the spectrum of the absorption cross section, (ii) the spectrum of the light pulse, and (iii) the selection of the wavelength band $\Lambda_1$.

One reason that the method is especially suitable for measurements in thermal devices is that thermal systems, when in use, typically comprise a lot of particles that scatter light. Thus such measurements can be easily performed. Moreover, inside a thermal device, the temperature is typically high. Therefore, molecules of the gaseous compounds inside the thermal device are in an exited state (i.e. a thermally excited state). The absorption spectra of these excited molecules comprise hot bands, which are typically more sensitive to temperature than the absorption spectra of the same gaseous compounds at the ground state at room temperature or lower. In this way, temperature in particular is easier to measure from a thermal device than from a gaseous compound at room temperature. Moreover, one of the assumptions in the method is that the backscattering factor β (cf. Eq. 3) is negligibly dependent on wavelength. This is typically the case, when the wavelength is short in comparison to the size of the scattering particles. It has been observed that the particle size in thermal devices is typically quite large, whereby a wavelength from 750 nm to 2000 nm has been seen to be suitable for these measurements. Therefore, in an embodiment, the first wavelength band $\Lambda_1$ or the second wavelength band $\Lambda_2$ comprises wavelengths from the range 750 nm to 2000 nm.

As discussed, for measuring the temperature profile, when only two wavelength bands are used, the molecular number density profile on the optical path of the light pulse may be assumed known, e.g. constant. However, preferably a third wavelength band is used to simultaneously measure the temperature T and molecular density N/V. A possible selection of these bands is shown in FIG. 4.

More generally, the third band can be used to measure two different quantities, such as temperature and molecular number density; or the third band can be used to measure the molecular number density, temperature, or pressure of another gaseous compound.

For example the third wavelength band can be used to measure two of temperature, pressure, and molecular number density. When e.g. temperature and molecular number density are measured, then two of the bands can be used to determine the temperature, as discussed above. For example the bands $\Lambda_1$ and $\Lambda_2$ of FIG. 4 can be used to determine the temperature, as depicted in FIGS. 3a and 3b. Other two can be used to determine the other quantity. For example the bands $\Lambda_2$ and $\Lambda_3$ of FIG. 4 can be used to determine the molecular number density. This embodiment of the method comprises selecting a third wavelength band $\Lambda_3$ using information on the spectrum of the absorption coefficient (or the absorption cross section) of the gaseous compound,
generating the pulse sequence such that the generated pulse sequence further comprises light for a third wavelength band $\Lambda_3$, wherein the third wavelength band $\Lambda_3$, is different from the first and the second wavelengths bands $\Lambda_1$ and $\Lambda_2$,
measuring, as function of time, the intensity of a scattered light pulse at the third wavelength band $\Lambda_3$,
providing information indicative of the intensity of the scattered light pulse at the third wavelength band $\Lambda_3$ as function of time,
determining information indicative of the differential absorption between at least two pairs of wavelength bands using the measured intensities, and
determining the temperature and the molecular number density of the gaseous compound as function of the distance from the location in the first direction using the information indicative of the differential absorption between at least two pairs of wavelength bands using the measured intensities.

The wavelength bands $\Lambda_1$, $\Lambda_2$, and $\Lambda_3$ are preferably optically separated. When optically separated, the wavelength bands $\Lambda_1$, $\Lambda_2$, and $\Lambda_3$ do not overlap. In other words, the intersection all the pairs of the wavelength bands are empty sets. Specifically the intersections of $\Lambda_1$ and $\Lambda_2$; $\Lambda_1$ and $\Lambda_3$; and $\Lambda_2$ and $\Lambda_3$ are empty sets or each comprise only one wavelength (an end point of $\Lambda_1$ and $\Lambda_2$; $\Lambda_1$ and $\Lambda_3$; or $\Lambda_2$ and $\Lambda_3$, respectively). However, in principle the wavelength bands may overlap. In this case, however, a wavelength band is not identical to another wavelength band, or identical to a union of some other wavelength bands. I.e. for example $\Lambda_1$ is different from $\Lambda_2$ and $\Lambda_3$, and also from $\Lambda_2 \cup \Lambda_3$.

With reference to FIG. 4, the wavelength bands may be selected in such a way, that one pair of wavelength bands (e.g. the first and the second) is used to determine the temperature, and that another pair of wavelength bands (e.g. the second and the third) is used to determine the molecular number density. The corresponding embodiment comprises selecting the first wavelength band such that the total attenuation factor for the pulse sequence, the first wavelength band, and the gaseous compound has a first value, and such that such that the total attenuation factor for the pulse sequence, the first wavelength band, and the gaseous compound depends on temperature in a first way,
selecting the second wavelength band such that the total attenuation factor for the pulse sequence, the second wavelength band, and the gaseous compound has a second value, and such that such that the total attenuation factor for the pulse sequence, the second wavelength band, and the gaseous compound depends on temperature in a second way
selecting a third wavelength band such that the total attenuation factor for the pulse sequence, the third wavelength band, and the gaseous compound has a third value, and such that such that the total attenuation factor for the pulse sequence, the third wavelength band, and the gaseous compound depends on temperature in a third way, wherein
the first way is different from the second way,
the second value is different from the third value, and
determining the temperature and the molecular density of the gaseous compound as function of the distance from the location in the first direction.

As is evident, the third wavelength band is a further wavelength band; further to the first and the second bands. The third band, or still further bands may be utilized alternatively, or in addition to determining the value of more quantities (temperature, pressure, molecular number density) regarding the gaseous compound 910, to determining the value of at least a quantity (temperature, pressure, molecular number density) regarding another gaseous compound of the gas mixture 900.

Referring to FIG. 4, the wavelength bands $\Lambda_3$ and $\Lambda_2$, for example, could be used to determine the molecular number density of steam, while the wavelength bands $\Lambda_3$ and $\Lambda_1$, for example, could be used to determine the molecular number density of carbon dioxide. As is evident, a further fourth band could be used to determine e.g. the temperature, in addition to the molecular number density of steam. A fifth band could be utilized to determine e.g. the temperature, in addition to the molecular number density of carbon dioxide. However, most likely the temperatures of different gaseous compounds should be equal, whereby multiple bands can be used to increase the accuracy. A corresponding embodiment comprises selecting a further wavelength band using information on the spectrum of the absorption cross section (or absorption coefficient) of a further gaseous compound, generating the pulse sequence also for the further wavelength band (i.e. such that the sequence comprises light from the further band), guiding the pulse sequence, from a location, in a first direction, into a thermal device, wherein the thermal device surrounds the gaseous mixture, the gaseous mixture comprising also the further gaseous compound and scattering particles, whereby the further gaseous compound absorbs at least part of the pulse sequence, and the particles of the gaseous mixture scatter at least part of the pulse sequence at various moments of time at least to a scattered light; the method comprising measuring, as function of time, the intensity of the scattered light at the third wavelength band, measuring, as function of time, the intensity of the scattered light at the first, the second, optionally also at third, and the further wavelength band, determining information indicative of the differential absorption between at least two pairs of wavelengths bands selected from the at least three wavelength bands using the measured intensities, and determining the temperature, the molecular number density, and/or the pressure of the further gaseous compound as function of the distance from the location in the first direction using the information indicative of the differential absorption between the two wavelengths bands.

As discussed, the light pulse source 110 may comprise a supercontinuum laser. Thereby, an embodiment of the method comprises generating a supercontinuum light pulse comprising light having multiple wavelengths in the first wavelength band $\Lambda_1$ and in the second wavelength band $\Lambda_2$; and optionally in the third or other further bands. Using such a light pulse 150 has the technical effect that the light pulse comprises continuously multiple wavelengths at both (or more generally all) wavelength bands. Compared to a conventional laser source, this has the technical effect that the wavelength of the light source needs not to be adapted to an absorption peak of the gaseous compound 910 to be measured. Moreover, if the width or location of the absorption peak changes e.g. due the changes in the temperature or pressure, and a conventional laser light source is used, the changes in the absorption peak have to be taken into account. As a supercontinuum light pulse 150 comprises continuously many wavelengths, the light pulse 150 will comprise light corresponding to the original absorption spectrum (at a first temperature) and light corresponding to the shifted absorption spectrum (at a second temperature). Thereby, the supercontinuum light source takes into account these changes, and provides for more robust measurements.

The detector arrangement 120 of the device 100 is arranged to measure the intensities (or optical powers; and at the at least two wavelength bands) at some time intervals $\Delta t$. The interval is defined by the sampling rate of the device. The interval may be e.g. from 10 ps to 10 ns. As an example, the sampling rate may be 1 GHz, whereby the time interval is 1 ns. However, as discussed above, during this time the pulse 150 can propagate only 15 cm and the backscattered pulse 160 another 15 cm. Therefore, a first spatial resolution is this case is about $(15\ cm)^{-1}$. The term "first spatial resolution" is here used, since the actual resolution may be decreased by other factors, as will be discussed. The term "resolution" in this case is given in terms of the inverse of the length, since in general, the denser the measurement interval, the better resolution. The first spatial resolution is therefore given as $res_1=(2/c)\times(1/\Delta t)$, wherein $1/\Delta t$ is the sampling frequency, and $\Delta t$ is the time between two subsequent measurements. Using a time interval of 10 ps (sampling frequency 100 GHz) increases the first spatial resolution to $(1.5\ mm)^{-1}$. Using a time interval of 10 ns (sampling frequency 100 MHz) decreases the first spatial resolution to $(1.5\ m)^{-1}$. In many practical cases, the vessel or device from which measurements are made have the size of some meters. Therefore, decreasing the sampling frequency even more would lead to too low a spatial resolution in comparison to the size of the vessel. However, theoretically there is no lower limit for the sampling frequency. Preferably the sampling frequency is selected such that at least five points are available for the determination of the profile. In this case the sampling frequency is at least $(5c)/(2L)$, wherein L is the length of the optical path the pulse 150 travels in the gaseous mixture 900. For example, L may correspond to a dimension (diameter, width, height, length) of a vessel, pipe, or device surrounding the gaseous mixture 900. Also preferably, the sampling rate at which the intensities of the scattered light pulses are detected is at least 100 MHz.

The spatial resolution of the method depends, on the other hand, on the (temporal) duration of the light pulse 150. The (temporal) duration of the pulse defines the (spatial) length of the light pulse, since the pulse travels at the speed of light. For example a 1 ns pulse has the spatial length of about 30 cm. Since the pulse 150 and the backscattered pulse 160 travel in the opposite directions, the resolution becomes twice as good as proposed only by the spatial length of the pulse 150. Therefore, a second spatial resolution is related to the (spatial) length of the pulse 150 as $res_2=(\frac{1}{2}ct_p)^{-1}$, wherein $t_p$ is the (temporal) duration of the pulse. The second spatial resolution, as defined above, is equal to inverse of half of the spatial length of the pulse. Therefore, by increasing the duration of the pulse, the length of the pulse increases, and the second spatial resolution decreases. For example, for 1 ns pulse the second spatial resolution is about $(15\ cm)^{-1}$. For example, for 10 ns pulse the second spatial resolution is about $(1.5\ m)^{-1}$. For example, for 10 ps pulse the second spatial resolution is about $(1.5\ mm)^{-1}$. Preferably the second spatial resolution is selected such that $L\times res_2 \geq 5$. More preferably the second spatial resolution is selected such that $L\times res_2 \geq 10$. Thereby, preferably the duration of the pulse $t_p$ is at most $(2L)/(5c)$. Also preferably, the duration of the light pulse is at most 10 ns. However, very short pulses are hard to generate. Thus, optionally, duration of the light pulse is at least 1 ps.

The spatial resolution furthermore depends on the pulse response of the detector arrangement 120. The pulse response of the detector arrangement, $t_{res}$, as discussed above, is preferably less than $t_p$. Even more preferably, $t_{res} < t_p/5$, or $t_{res} < t_p/10$. This being the case, the pulse response of the detector arrangement limits the spatial resolution only negligibly. However, in some cases the duration of the light pulse may be very short, whereby even a longer pulse response of the detector arrangement 120 provides for a sufficient spatial accuracy. In such cases, the pulse response of the detector arrangement 120, $t_{res}$, can be e.g. less than 5 ns, less than 1 ns, or less than less than 0.2 ns.

The overall spatial resolution obtainable from the measurements is the smaller of the first and the second spatial resolutions. For example, a 1 GHz sampling frequency gives the first spatial resolution of $(15 \text{ cm})^{-1}$, and a 1 ns light pulse gives the second spatial resolution of $(15 \text{ cm})^{-1}$. Thus overall spatial resolution is about $(15 \text{ cm})^{-1}$. Preferably the (spatial) length of the pulse is at most one fifth (⅕) of the length L of the first optical path. Typical examples of the length L include 1 m, 5 m, 10 m, and 20 m. Moreover, preferably the sampling frequency is selected such that only the length of the pulse limits the measurement resolution. Generally in signal processing, the sampling frequency should be twice the physical frequency. Therefore, preferably $\Delta t \le \frac{1}{2} t_p$. Even more preferably the sampling frequency is high enough to enable some data processing (e.g. filtering and averaging), whereby even more preferably $\Delta t \le t_p/10$.

The energy of the pulse 150 should be reasonably high to obtain results from the scattered pulse 160. The energy refers to the energy of an un-attenuated pulse, i.e. the pulse that the light pulse source 110 generates. Preferably the energy of the light pulse is at least 0.01 μJ or at least 0.1 μJ. Preferably the energy of the light pulse is at least 0.01 μJ or at least 0.1 μJ for each wavelength band. Optionally, the energy of the pulse 150 may be at most 1 J. The energy refers to the energy generated by the light pulse source 110. As discussed above, the energy of the pulse decreases as it travel through the space containing the gaseous mixture 900.

In a preferred embodiment, the method is used to determine the temperature and/or the molecular number density inside a thermal device 200. The term "thermal device" 200 refers to a device that is arranged to produce energy and/or fuel. Preferably the thermal device 200 is arranged to produce heat and/or fuel. Preferably the thermal device 200 is arranged to produce heat. The thermal device may comprise one of a boiler, a pyrolysis reactor, a torrefaction reactor, or a gasifier. The boiler may be a fluidized bed boiler. The fluidized bed boiler may be a bubbling fluidized bed boiler or a circulating fluidized bed boiler.

The method is particularly suitable for measurements inside a thermal device since

- the temperature inside a thermal device is high, whereby the measurement equipment should be located outside the thermal device, and therefore optical methods are preferred;
- the temperature gradients are typically reasonably high, whereby the measurement accuracy is reasonable for obtaining a temperature profile;
- the temperature inside a thermal device is high, whereby the molecules of the gaseous compounds inside the thermal device are in an exited state (i.e. a thermally excited state), whereby the absorption spectra of these excited molecules comprise hot bands, which are typically more sensitive to temperature than the absorption spectra of the same gaseous compounds at the ground state at room temperature or lower, whereby temperature in particular is easier to measure from hot gas; and
- the gaseous mixture 900 inside a thermal device 200 typically comprises particles 920 that scatter the light pulse 150; whereby the aforementioned method is particularly suitable for gaseous mixtures 900 produced by and in a thermal device.

Wavelengths especially suitable for thermal devices were discussed above.

As is evident for a person skilled in the art, statistical methods may be applied to improve the accuracy of the measurements. An embodiment of the method comprises

- generating multiple light pulses, optionally in such a way that the time difference between two subsequent light pulses is at least 15 ns,
- guiding, from the location, the light pulses to the gaseous mixture in the first direction,
- measuring, as function of time, the intensities of the scattered light pulses at the first wavelength band and at the second wavelength band,
- providing information indicative of the intensities of the scattered light pulses at the first and second wavelength bands as function of time,
- determining the temperature, pressure, and/or the molecular number density of the gaseous compound as function of the distance from the location in the first direction using a statistical method and the information indicative of the intensities of the scattered light pulse at the first and the second wavelength bands as function of time.

Naturally, a third wavelength band can be used to measure e.g. temperature and molecular number density. Further wavelength bands may be used to measure e.g. temperature and/or molecular number density of two different gaseous compounds.

The number of the multiple light pulses may be selected according to the accuracy requirements. The time difference between two subsequent pulses should be selected in such a way that only one light pulse 150 at a time propagates in the first direction $D_1$ in the space comprising the gaseous mixture 900. Naturally the scattered light pulse 160 propagates in the scape as well, but not in the first direction. As discussed above, the space in which the gaseous mixture 900 is typically located has a dimension of 1 m to 20 m. Thereby, the time difference between two subsequent light pulses may be e.g. at least 15 ns, corresponding to a dimension of 5 m; at least 3 ns, corresponding to a dimension of 1 m; or at least 60 ns, corresponding to a dimension of 20 m.

The method, as discussed above, results in the temperature, pressure, and/or molecular number density information along an optical path in a space. However, in addition or alternatively to the statistical techniques, multiple pulses 150 may be generated in the method and guided to the space into different directions. Thereby information from many optical paths can be obtained. In this way, information on the temperature and/or the molecular number density can be obtained e.g. from a two-dimensional plane and/or a three-dimensional volume. This information can be obtained via a single inlet 205 (cf. FIG. 1c).

In an embodiment, a first light pulse 150 is guided to the first direction $D_1$ onto an optical path; wherein the light pulse 150 travels along the optical path. If the pulse 150 does not meet a reflector or boundaries between optically different materials, the optical path is straight. After detecting the intensities of the scattered light pulse 160, a second light pulse 150 is guided to a second optical path. In principle it would be possible to have parallel optical paths and multiple devices. However, the direction can be easily varied, e.g. by a reflector (mirror), of which angle or angles is/are arranged to be variable with respect to the space comprising the gaseous mixture 900, such as the wall 204 of a vessel, a pipe, or a thermal device. Thus, preferably in the method a second light pulse 150 is guided to a second direction $D_2$ onto a second optical path, wherein the second direction $D_2$ forms an angle (i.e. non-zero angle) with the first direction $D_1$.

Referring to FIGS. 1a and 1c, FIG. 1a shows the measurement, when the light pulse 150 or pulse sequence is guided to the first direction $D_1$. FIG. 1c shows the subsequent method step, wherein a second optical pulse 150b or pulse sequence is guided to a second direction $D_2$. When the second light pulse 150b hits a particle 920, a part of the second pulse backscatters as the scattered pulse 160b. A part 152b of the second pulse 150b continues along the second optical path.

This embodiment comprises
  generating for a first wavelength band and a second wavelength band a further pulse sequence comprising a light pulse or light pulses; wherein preferably the same wavelength bands and/or light pulse source(s) 110 is/are used as in the previous method step,
  guiding, from the location O, the further pulse sequence to the gaseous mixture 900 in the thermal device in a second direction $D_2$, wherein the second direction forms an angle with the first direction, whereby
    the molecules of the gaseous compound 910 absorb at least part of the at least one of the further pulse sequence,
    particles 920 of the gaseous mixture 900 scatter at least part of the further pulse sequence to scattered further light; the method comprising
  measuring, as function of time, the intensity of the scattered further light at the first wavelength band $\Lambda_1$, and at the second wavelength band $\Lambda_2$,
  determining information indicative of the differential absorption between the two wavelengths bands using the intensities,
  determining the temperature, pressure, and/or the molecular number density of the gaseous compound as function of the distance from the location in the second direction using the information indicative of the differential absorption between the two wavelengths bands.

Also in this embodiment, preferably the backscattered light pulse is used. I.e. the detector 120 is arranged to detect a backscattered second light pulse(s) 160b; whereby the backscattered second light pulse 160b propagates in a direction that is reverse to the direction of propagation of the second light pulse 150b. Also in this embodiment a light pulse comprising light having at least three wavelength bands can be used.

Preferably light pulses are guided to multiple directions, whereby a profile of the temperature and/or molecular number density can be obtained. A corresponding method comprises
  generating multiple light pulse sequences,
  guiding, from the location O, the multiple light pulse sequences to the gaseous mixture in different directions ($D_1$, $D_2$); at least one pulse sequence to a direction, and optionally many pulses to a direction, and
  determining the temperature and/or the molecular number density of the gaseous compound as function of the distance from the location in the different directions, optionally using statistical means, thereby obtaining a two-dimensional or a three-dimensional profile of the temperature, pressure, and/or the molecular number density. As discussed, preferably a three-dimensional profile of temperature or molecular number density, or three-dimensional profiles of temperature and molecular number density, are obtained.

In the above, multiple pulse sequences may be guided to a direction, whereby statistical methods can be used to improve the accuracy of measurements in this direction. What is important in this embodiment is that at least one pulse sequence is guided to a direction, and the number of different directions to which a pulse sequences are guided is reasonably large; e.g. at least 5, at least 25, at least 50, or at least 100 to obtain a two dimensional, preferably three dimensional, profile.

The corresponding system may comprise a reflector 172 (such as a mirror), of which angle is arranged variable with respect to the space comprising the gaseous mixture. Possibly, the reflector is fixed with respect to the light pulse source 110 and the detector 120, and the whole device 100 is arranged to be turned. In a preferred embodiment, other components of the device 100 may be arranged fixed with respect to the space comprising the gaseous mixture (e.g. the interior of a thermal device 200), whereby the angle (or the angles) of the reflector 172 is (are) arranged variable e.g. with respect of the detector 120 and/or the light pulse source 110. The position of the reflector 172 is determined by two angles. In case only one of these angles is arranged changeable, while the other is constant, the direction for the optical pulse can be changed in such a way that a two-dimensional profile of the temperature, pressure, and/or the molecular number density can be obtained. More preferably, the two angles of the reflector 172 are arranged changeable with respect to the space comprising the gaseous mixture 900 (e.g. with respect to the thermal device 200 and/or the wall 204 of the thermal device and/or the light pulse source 110 and/or the detector 120). By varying these two angles, a three-dimensional profile of the temperature, pressure, and/or the molecular number density is obtainable.

Figure 5:
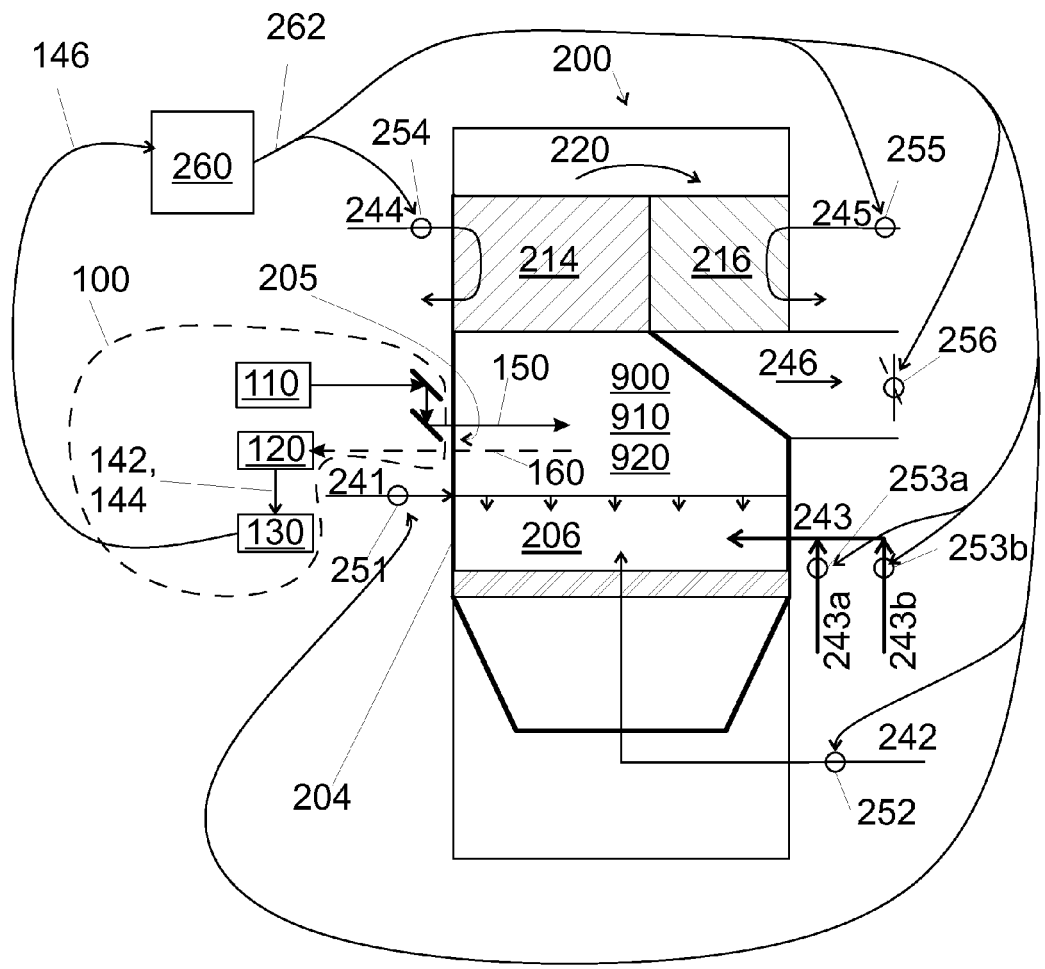
FIG. 5 shows a thermal system comprising a thermal device; a device for measuring the temperature, pressure, and/or the molecular number density; and a controller for controlling the operation of the thermal device.

FIG. 5 shows, as an example, a thermal system comprising a thermal device 200 and a device 100 for measuring temperature, pressure, and/or molecular number density. FIG. 5 shows a boiler 200. The boiler 200 comprises a furnace 206. On top of the furnace 206, a superheater area 214 and an economizer area 216 are located. Material to be burnt, which is referred to as fuel mix, such as biomass and/or waste, is fed to the furnace by the feeding means 243. A first part of the fuel mix, such as biomass (and/or waste material), is fed to the feeding means 243 by the feeding means 243a. A second part of the fuel mix, such as coal (and/or peat), is fed to the means 243 by the feeding means 243b. Alternatively, the means 243a and 243b could feed the corresponding material directly to the furnace 206. It is evident, that even if two types of material may be fed to the furnace with the equipment of FIG. 5, a system wherein the embodiments of the present invention are applicable, may comprise means for feeding only one type of material to be burnt. It is also evident, that the fuel mix may comprise more than two types of material to be burnt. Typically the composition of the fuel mix is adjusted to adjust the sulfur content of the fuel mix, and thereby affecting the properties of the flue gas. Compositions of the fuel mix may include biomass and coal; biomass and peat; waste material and coal; and waste material and peat. Any or all of the aforementioned feeding means 243, 243a, and 243b, may comprise a conveyor, such as a screw conveyor or a belt conveyor.

In addition, air is supplied to the furnace by the feeding means 242. The feeding means 242 may comprise a pipe and/or a nozzle. Moreover, additive material is supplied using the feeding means 241. The additive material may be solid material or comprised by a liquid solution. The feeding means 241 may comprise at least one of a conveyor (e.g. screw or belt conveyor), a pipe and/or a nozzle. As the boiler 200 produces energy in the form of heat, heat is recovered. Heat is recovered e.g. in a superheater, located in the superheater area 214. The superheater recovers heat to a heat transfer medium, such as water. The feeding means 244, such as a pipe, is used to feed the heat transfer medium to a superheater. Heat can also be recovered in an economizer, located in the economizer area 216. The economizer recovers heat to the (or another) heat transfer medium, such as water. The feeding means 245, such as a pipe, is used to feed the (or the another) heat transfer medium to the economizer. In between the superheater 214 area and the economizer area 216 the flue gases flow in a channel. The flue gas flow is depicted with the arrow 220. Still further, the flue gases are let out from the process. The arrow 246 depicts the flue duct in which the flue gas flows out of the thermal device 200.

It is noted that in some other thermal devices, such as a torrefaction reactor, air is not supplied to the thermal device. Moreover, additive material is not necessarily fed to the thermal device.

The thermal system of FIG. 5 further comprises at least one means for controlling a flow into or out of the thermal device 200. The means for controlling a flow may be referred to as a flow controller. Referring to FIG. 5, the term "flow controller" include

- the means 251 for controlling the flow of the additive material. The means 251 may comprise a valve for controlling liquid additive material or a motor of a conveyor for controlling the speed of the conveyor for the (solid) additive material.
- the means 252 for controlling the flow of air, such as a valve.
- the first means 253a such as a motor of a conveyor 243a for controlling the flow of the first material to be burnt.
- the second means 253b such as a motor of a conveyor 243b for controlling the flow of the second material to be burnt.
- the means 254 for controlling the flow and/or temperature of the heat transfer medium 244 into a superheater. The means 254 may comprise at least one of a valve, a heater, a cooler, and a heat exchanger. By controlling the feed of the heat transfer medium to a superheater, the flow of energy out of the thermal device 200 is controlled. In addition to the flow, the temperature of the heat transfer medium can be controlled.
- the means 255 for controlling the flow and or temperature of the heat transfer medium 245 into an economizer. The means 255 may comprise at least one of a valve, a heater, a cooler, and a heat exchanger. By controlling the feed of the heat transfer medium to an economizer, the flow of energy out of the thermal device 200 is controlled. In addition to the flow, the temperature of the heat transfer medium can be controlled.
- the means 256 for controlling the flow of flue gas 246 out of the thermal device 200. The means 256 may comprise at least one of a valve, and a damper. By controlling the flow of the flue gas 300, the temperature and/or pressure in the furnace can be controlled.

By using at least one of these means 251-256, also the temperature and/or the pressure inside the thermal device 200 can be controlled. Any or all of the flow controllers 251 to 256 may be arranged to receive a signal 262 from a controller 260, and arranged, using this signal, to control the corresponding flow. The controller 260 is arranged to control a flow controller (251, 252, 253a, 253b, 254, 255, 256). The controller 260 may receive information 146 indicative of the temperature and/or the molecular number density (one, two or three dimensional profile) from the processing unit 130. The controller 260 may be integrated with the processing unit 130. At least some of the light pulse source 110, the detector arrangement 120, the processing unit 130 and the controller 260 may be integrated together.

The corresponding method comprises
- determining the temperature, pressure, and/or the molecular number density of the gaseous compound as function of the distance from the location in the first direction as described above,
- providing information 146 indicative of the temperature, pressure, and/or the molecular number density, and
- controlling the thermal process using the information 146 indicative of the temperature, pressure, and/or the molecular number density.

Figure 6A:
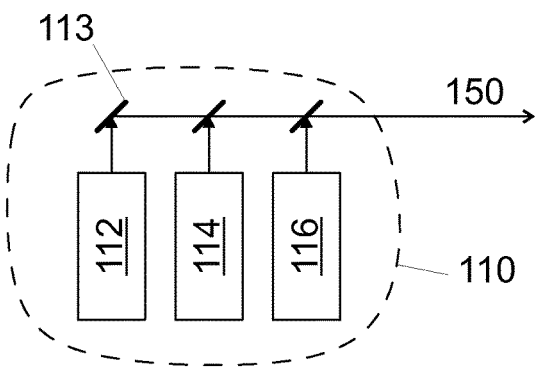
FIG. 6a shows a light pulse source arrangement.

As for further details of the device 100, FIG. 6a shows an embodiment of a light pulse source 110 comprising three conventional lasers. As is clear from the above discussion, a light pulse source 100 comprising two conventional lasers suffices for some embodiments. Referring to FIG. 6a, the light pulse source 110 may comprise at least two lasers 112 and 114, and optionally more lasers, such as the laser 116. Still further, the light pulse source may comprise at least one optical element 113 arranged to generate a light pulse 150 comprising light having the first wavelength and light having the second wavelength, wherein the first wavelength is different from the second wavelength. As the optical element 113, a reflector or a wavelength sensitive reflector may be used. As discussed above, alternatively, and preferably, the device 100 comprises a supercontinuum light pulse source.

Figure 6B:
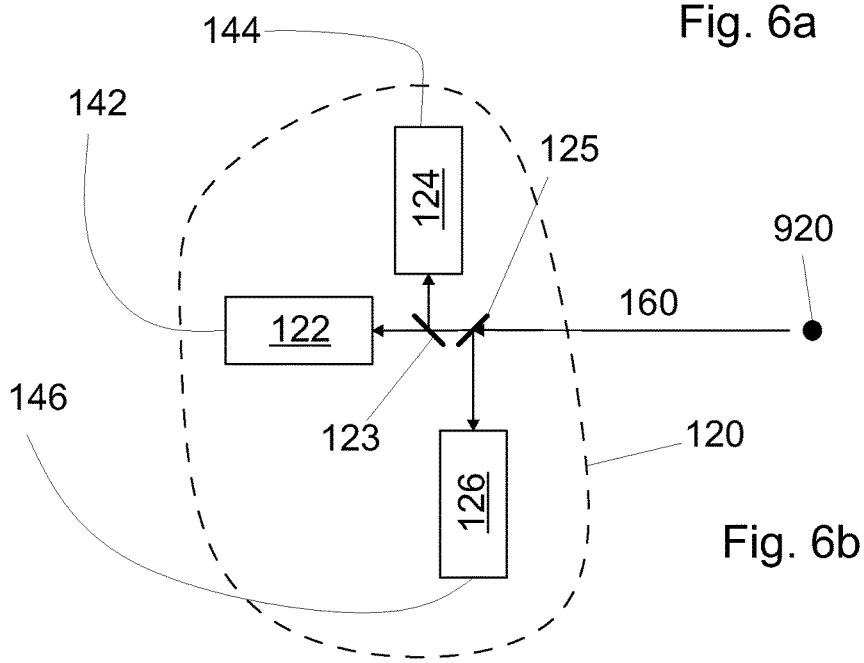
FIG. 6b shows a detector arrangement.

As for further details of the device 100, FIG. 6b shows an embodiment of a detector arrangement 120 comprising three photodetectors 122, 124, 126 and two beam splitters 123, 125. As is evident, a detector arrangement 120 may comprise only two photodetectors (e.g. 122, 124) and one beam splitter (e.g. 123). Two photodetectors suffice for the wavelength band selections of FIGS. 2a and 3a; however three photodetectors may be deeded for the selections of FIG. 4. In principle, a single photodetector could measure the spectral intensity, whereby the division of the intensity to the first optical band $\Lambda_1$ and the second optical band $\Lambda_2$ could be made in the processing unit 130. However, currently the optical splitting of the scattered pulse 160 to different wavelength bands using at least one beam splitter is economically more feasible.

Referring to FIG. 6b, the beam splitter(s) and the photodetectors may be arranged in such a manner that the distance from the scattering particle 920 to all photodetectors 122, 124, 126 along the corresponding optical path is the same. This improves the spatial accuracy, as the time of flight of the light pulse 150, from the light pulse source 110 to all the photodetectors 122, 124, 126 of the detector 120 is the same. In FIG. 6b, e.g. the distance from the beam splitter 125 to the photodetector 126 is the same as the distance from the beam splitter 125 to the photodetector 122 (both the corresponding optical paths are straight from the beam splitter). Moreover, the distance from the beam splitter 125 to the photodetector 124, via the path that a part of the scattered light pulse 160 travels, is the same.

A beam splitter, e.g. the beam splitter 123, may be arranged to reflect light corresponding to the second wavelength band $\Lambda_2$ and pass light corresponding to the first wavelength band $\Lambda_1$. In case more than two wavelength bands are used, another beam splitter 125 may be arranged to reflect light corresponding to the third wavelength band $\Lambda_3$ and pass light corresponding to other wavelength bands; i.e. the first wavelength band $\Lambda_1$ and the first wavelength band $\Lambda_2$. Therefore, an embodiment of the device 100 comprises a beam splitter 123 arranged to divide at least a part of the scattered light pulse 160 to a first part comprising light corresponding to the first wavelength band $\Lambda_1$ and to a second part comprising light corresponding to the second wavelength band $\Lambda_2$. Referring to FIG. 6b, in an embodiment other wavelength bands are guided away from the scattered pulse 160 before the beam splitter 123. Therefore, the beam splitter 123 is arranged to divide only a part of the scattered pulse 160 to two parts. Naturally, any or many of the wavelength bands can be separated from the scattered pulse 160 by a beam splitter that the scattered pulse 160 hits first. Thereafter, subsequent beam splitters may be used to further divide the remaining part of scattered pulse 160. For example, the first beam splitter 125 could be used to separate light of the first wavelength band $\Lambda_1$ from the rest of the pulse. In that case already the first beam splitter would be arranged to divide the (whole) scattered light pulse 160 to a first part comprising light corresponding to the first wavelength band $\Lambda_1$ and a to a second part comprising light corresponding to the second wavelength band $\Lambda_2$. It is noted that in this case the second part would further comprise light corresponding to the third wavelength band $\Lambda_3$.

The first photodetector 122 is arranged to provide information 142 indicative of the intensity of the scattered light pulse 160 at the first wavelength band $\Lambda_1$ as function of time. The second photodetector 124 is arranged to provide information 144 indicative of the intensity of the scattered light pulse 160 at the second wavelength band $\Lambda_2$ as function of time. In FIG. 6b, the third photodetector 126 is arranged to provide information 146 indicative of the intensity of the scattered light pulse 160 at the third wavelength band $\Lambda_3$ as function of time.

For scanning the temperature and/or molecular number density profile the device 100 may comprise
 a reflector 172 for guiding the light pulse to the gaseous mixture, in to at least the first direction $D_1$, wherein
 at least an angle of the reflector 172 is arranged changeable (e.g. with respect to the detector 120 and/or the thermal device 200), whereby the direction in to which the light pulse is guided is arranged changeable.

The reflector 172 may be located at the location O, or in the vicinity of the location. The location O may be e.g. a point on the reflector 172, or the surface of the reflector 172. As discussed above, in an embodiment only one angle of the reflector 172 is arranged changeable, whereby a two-dimensional profile is measurable. Preferably, and in an embodiment, two different angles of the reflector 172 are arranged changeable, whereby a three-dimensional profile is measurable.

The device 100 forms a part of a thermal system. An embodiment of a thermal system comprises
 a device 100 for measuring temperature and/or molecular number density of a gaseous compound as function of distance from a gaseous mixture comprising the gaseous compound and scattering particles, the gaseous compound attenuating and scattering at least some light, as described above, and
 a thermal device 200, such that
 the device 100 is arranged to guide the light pulse 150 into the thermal device 100.

In this way, the temperature and/or molecular number density can be measured from the interior of the thermal device. The device 100 can be located outside the thermal device. An embodiment comprises
 a wall 204 separating the interior of the thermal device 200 from the exterior of the thermal device, and
 an optical inlet 205 arranged in the wall 204, wherein
 the gaseous mixture 900 is arranged in the interior of the thermal device 200, and
 the device 100 is arranged in the exterior of the thermal device 200.

As discussed, a thermal system may be arranged to control the thermal process performed in the system (particularly in the thermal device 200 of the thermal system). Such a thermal system comprises
 a controller 260, wherein
 the processing unit 130 is arranged to provide information 146 indicative of the temperature and/or the molecular number density of the gaseous, compound 910 and
 the controller 260 is arranged to control a flow into or out of the thermal device 200 using the information 146 provided by the processing unit 130.

EXAMPLES

1. A method for measuring temperature, molecular number density, and/or pressure of a gaseous compound as function of distance, the gaseous compound absorbing at least some light, the method comprising
 selecting a first wavelength band and a second wavelength band using information on the spectrum of the absorption coefficient of the gaseous compound and/or the temperature dependence thereof,
 generating, for the first wavelength band and the second wavelength band, a pulse sequence comprising a light pulse or light pulses,
 guiding the pulse sequence, from a location, in a first direction, into a thermal device, wherein the thermal device surrounds some gaseous mixture, the gaseous mixture comprising the gaseous compound and scattering particles, whereby
 molecules of the gaseous compound absorb at least part of the light pulse or at least part of at least one of the light pulses, and
 particles of the gaseous mixture scatter at least part of the light pulse or at least part of the light pulses at various moments of time at least to scattered light;
 the method comprising
 measuring, as function of time, the intensity of the scattered light at the first wavelength band,
 measuring, as function of time, the intensity of the scattered light at the second wavelength band,
 determining information indicative of the differential absorption between the two wavelengths bands using the intensity of the scattered light at the first wavelength band and the intensity of the scattered light at the second wavelength band, and
 determining the temperature, the molecular number density, and/or the pressure of the gaseous compound as function of the distance from the location in the first direction using the information indicative of the differential absorption between the two wavelengths bands.

2. The method of example 1, comprising
 selecting a wavelength band such that the molecular absorptance or the expected molecular absorptance for the wavelength band is at least 1%;

optionally selecting another wavelength band such that the molecular absorptance or the expected molecular absorptance for the other wavelength band is at most 99%.

3. The method of example 1 or 2, comprising
selecting the first wavelength band such that the total attenuation factor for the pulse sequence, the first wavelength band, and the gaseous compound has a first value,
selecting the second wavelength band such that the total attenuation factor for the pulse sequence, the second wavelength band, and the gaseous compound has a second value, wherein
the first value is different from the second value; preferably (i) at a temperature, the smallest total attenuation factor is less than $10^{-23}$ cm$^2$ or (ii) at a temperature, the ratio of the greatest total attenuation factor to the smallest total attenuation factor is at least 2, and
determining the molecular number density of the gaseous compound as function of the distance from the location in the first direction.

4. The method of example 1 or 2, comprising
selecting the first wavelength band such that the total attenuation factor for the pulse sequence, the first wavelength band, and the gaseous compound depends on temperature in a first way,
selecting the second wavelength band such that the total attenuation factor for the pulse sequence, the second wavelength band, and the gaseous compound depends on temperature in a second way, wherein
the first way is different from the second way; preferably at least one total attenuation factor has an absolute temperature dependence of at least 100 ppm/K, and
determining the temperature of the gaseous compound as function of the distance from the location in the first direction.

5. The method of any of the examples 1 to 4, wherein
the gaseous compound comprises at least one of steam ($H_2O$), oxygen ($O_2$), carbon dioxide ($CO_2$), carbon monoxide (CO), ammonia ($NH_3$), nitrogen oxide ($NO_X$), and sulfur oxide ($SO_X$); preferably the gaseous compound comprises steam ($H_2O$) or carbon dioxide ($CO_2$).

6. The method of any of the examples 1 to 5, wherein
the temperature of the gaseous compound is at least 400° C.; and optionally the temperature of the gaseous compound is at most 1200° C.

7. The method of any of the examples 1 to 6, wherein
the first wavelength band or the second wavelength band comprises wavelengths from the range 750 nm to 2000 nm and/or
the linear size of the space is at most 50 m and/or
the duration of a light pulse of the pulse sequence is at most 10 ns, optionally at least 1 ps; the sampling rate at which the intensities of the scattered light is detected is at least 100 MHz; and the pulse response of a detector arrangement used for the measuring of the intensity is less than 5 ns, optionally less than 1 ns and/or
the energy of a light pulse of the pulse sequence is at least 0.01 μJ, optionally at most 1 J.

8. The method of any of the examples 1 to 7, comprising
generating a supercontinuum light pulse comprising light having continuously multiple wavelengths in the first wavelength band and in the second wavelength band such that the pulse sequence comprises the supercontinuum light pulse.

9. The method of any of the examples 1 to 8, comprising
generating, for a first wavelength band and a second wavelength band, a further pulse sequence comprising a light pulse or light pulses,
guiding, from the location, the further pulse sequence into the thermal device in a second direction, wherein the second direction forms an angle with the first direction, whereby
molecules of the gaseous compound absorb at least part of the light pulse or at least part of the light pulses of the further pulse sequence, and
particles of the gaseous mixture scatter at least part of the light pulse or at least part of the light pulses of the further pulse sequence at various moments of time at least to a scattered further light; the method comprising
measuring, as function of time, the intensity of the scattered further light at the first wavelength band,
measuring, as function of time, the intensity of the scattered further light at the second wavelength band,
determining information indicative of the differential absorption between the two wavelengths bands using the intensities of the scattered further light, and
determining the temperature, pressure, and/or the molecular number density of the gaseous compound as function of the distance from the location in the second direction using the information indicative of the differential absorption between the two wavelengths bands for the scattered further light.

10. The method of example 9, comprising
generating multiple pulse sequences,
guiding, from the location, the multiple pulse sequences in to the thermal device in different directions; at least one pulse sequence to a direction, and
determining the temperature, pressure, and/or the molecular number density of the gaseous compound as function of the distance from the location in the different directions, optionally using statistical means, thereby obtaining a two-dimensional or a three-dimensional profile of the temperature, pressure, and/or the molecular number density.

11. The method of any of the examples 1 to 10 comprising
selecting a further wavelength band using information on the spectrum of the absorption coefficient of the gaseous compound,
generating the pulse sequence also for the further wavelength band,
measuring, as function of time, the intensity of the scattered light at the further wavelength band,
determining information indicative of the differential absorption between at least two pairs of wavelengths bands selected from the three wavelength bands using the measured intensities, and
determining, as function of the distance from the location in the first direction using the information indicative of the differential absorption, at least two of the temperature, the molecular number density, and the pressure of the gaseous compound.

12. The method of example 11, wherein the further wavelength band forms a third wavelength band, the method comprising
selecting the first wavelength band such that the total attenuation factor for the pulse sequence, the first wavelength band, and the gaseous compound has a first value, and such that such that the total attenuation factor for the pulse sequence, the first wavelength band, and the gaseous compound depends on temperature in a first way, selecting the second wavelength band such that the total attenuation factor for the pulse sequence, the second wavelength band, and the gaseous compound has a second value, and such that such that the total attenuation factor for the pulse sequence, the second wavelength band, and the gaseous compound depends on temperature in a second way selecting the third wavelength band such that the total attenuation factor for the pulse sequence, the third wavelength band, and the gaseous compound has a third value, and such that such that the total attenuation factor for the pulse sequence, the third wavelength band, and the gaseous compound depends on temperature in a third way, wherein the first way is different from the second way, and the second value is different from the third value, the method comprising determining the temperature and the molecular number density of the gaseous compound as function of the distance from the location in the first direction.

13. The method of any of the examples 1 to 12 comprising selecting a further wavelength band using information on the spectrum of the absorption coefficient of a further gaseous compound, generating the pulse sequence also for the further wavelength band, measuring, as function of time, the intensity of the scattered light at the further wavelength band, determining information indicative of the differential absorption between at least two pairs of wavelengths bands selected from the at least three wavelength bands using the measured intensities, and determining the temperature, the molecular number density, and/or the pressure of the further gaseous compound as function of the distance from the location in the first direction using the information indicative of the differential absorption between the two wavelengths bands.

14. A method for controlling a thermal process, the method comprising determining the temperature, the molecular number density, and/or the pressure of the gaseous compound as function of the distance from the location in the first direction according to the method of any of the examples 1 to 13, providing information indicative of the temperature, the molecular number density, and/or the pressure, and controlling the thermal process using the information indicative of the temperature, the molecular number density, and/or the pressure.

15. A thermal system comprising a thermal device comprising at least a member limiting a space, the member having an optical inlet, wherein, in use, the space is arranged to contain some gaseous mixture comprising some gaseous compound and scattering particles, the gaseous molecules of the compound absorbing at least some light at least at a first wavelength band or a second wavelength band and the scattering particles scattering at least some light at least at a first wavelength band or a second wavelength band; the system comprising a light pulse source arrangement arranged to generate, for the first wavelength band and the second wavelength band, a pulse sequence comprising a light pulse or light pulses, means for guiding, from a location, to a first direction, the pulse sequence into the space through the optical inlet, whereby molecules of the gaseous compound absorb at least part of at least one of the light pulses and the particles of the gaseous mixture scatter at least part of the light pulse or at least part of the light pulses to scattered light, a detector arrangement arranged to measure, as function of time, the intensity of the scattered light at the first wavelength band and at the second wavelength band, and a processing unit for determining the temperature, the molecular number density, and/or the pressure of the gaseous compound as function of the distance from the location in the first direction using the measurement results of the detector by determining information indicative of the differential absorption between the two wavelengths bands using the information provided by the detector arrangement.

16. The thermal system of example 15, wherein the member or another member limiting the space of the thermal device comprises heat exchange pipes to recover heat from the member by convection and/or the linear size of the space is from 2 m to 50 m.

17. The thermal system of example 15 or 16, wherein the detector arrangement comprises a beam splitter arranged to divide at least a part of the scattered light to a first part comprising light corresponding to the first wavelength band and to a second part comprising light corresponding to the second wavelength band.

18. The thermal system of any of the examples 15 to 17, wherein the light pulse source arrangement comprises a supercontinuum light pulse source.

19. The thermal system of any of the examples 15 to 18, comprising a reflector for guiding the pulse sequence to the gaseous mixture, wherein at least an angle of the reflector is arranged changeable, whereby the direction in to which the pulse sequence is guided is arranged changeable.

20. The thermal system of any of the examples 15 to 19, comprising a controller, wherein the processing unit is arranged to provide information indicative of the temperature, pressure, and/or the molecular number density of the gaseous compound, and means for providing the information indicative of the temperature, the molecular number density, and/or the pressure to the controller, wherein the controller is arranged to control a flow into or out of the thermal device using the information provided by the processing unit.

The invention claimed is:

1. A method for measuring at least a temperature and molecular number density of a gaseous compound as a function of distance, the gaseous compound absorbing at least some light, the method comprising:

selecting a first wavelength band, a second wavelength band, and a third wavelength band using information on a spectrum of an absorption coefficient of the gaseous compound and/or the temperature dependence thereof;

generating, for the first wavelength band, the second wavelength band, and the third wavelength band, a pulse sequence comprising a light pulse or light pulses, wherein the pulse sequence comprises a supercontinuum light pulse comprising light having continuously multiple wavelengths in the first wavelength band and the second wavelength band;

guiding the pulse sequence into a thermal device, wherein the thermal device surrounds some gaseous mixture, the gaseous mixture comprising the gaseous compound and scattering particles, whereby molecules of the gaseous compound absorb at least part of the light pulse or at least part of at least one of the light pulses, and the scattering particles of the gaseous mixture scatter at least part of the light pulse or at least part of the light pulses of the pulse sequence at various moments of time at least to produce scattered light;

measuring, as a function of time, the intensity of the scattered light at the first wavelength band, the second wavelength band, and the third wavelength band;

determining information indicative of a differential absorption between at least two pairs of wavelengths bands selected from the three wavelength bands using the intensity of the scattered light at the first wavelength band, the intensity of the scattered light at the second wavelength band, and the intensity of the scattered light at the third wavelength band; and determining, as a function of the distance using the information indicative of the differential absorption, at least the temperature and the molecular number density of the gaseous compound.

2. The method of claim 1, further comprising:
selecting a wavelength band such that a molecular absorptance or an expected molecular absorptance for the wavelength band is at least 1%; and
selecting another wavelength band such that a molecular absorptance or an expected molecular absorptance for the other wavelength band is at most 99%.

3. The method of claim 1, further comprising:
selecting the first wavelength band such that a total attenuation factor for the pulse sequence, the first wavelength band, and the gaseous compound has a first value; and
selecting the second wavelength band such that the total attenuation factor for the pulse sequence, the second wavelength band, and the gaseous compound has a second value, wherein
the first value is different from the second value, and
the molecular number density of the gaseous compound is determined as a function of the distance.

4. The method of claim 1, further comprising:
selecting the first wavelength band such that a total attenuation factor for the pulse sequence, the first wavelength band, and the gaseous compound depends on the temperature in a first way; and
selecting the second wavelength band such that the total attenuation factor for the pulse sequence, the second wavelength band, and the gaseous compound depends on the temperature in a second way, wherein
the first way is different from the second way, and
the temperature of the gaseous compound is determined as a function of the distance.

5. The method of claim 1, wherein
the gaseous compound comprises at least one of steam ($H_2O$), oxygen ($O_2$), carbon dioxide ($CO_2$), carbon monoxide (CO), ammonia ($NH_3$), nitrogen oxide ($NO_x$), and sulfur oxide ($SO_x$).

6. The method of claim 1, wherein
the first wavelength band or the second wavelength band comprises wavelengths from the range 750 nm to 2000 nm, and/or
a linear size of the space is at most 50 m, and/or
the duration of a light pulse of the pulse sequence is at most 10 ns, a sampling rate at which the intensities of the scattered light is detected is at least 100 MHZ, and the pulse response of a detector arrangement used for the measuring of the intensity of the scattered light is less than 5 ns, and/or
the energy of a light pulse of the pulse sequence is at least 0.01 µJ, and at most 1 J.

7. The method of claim 1, further comprising:
selecting the first wavelength band such that a total attenuation factor for the pulse sequence, the first wavelength band, and the gaseous compound has a first value, and such that the total attenuation factor for the pulse sequence, the first wavelength band, and the gaseous compound depends on the temperature in a first way;
selecting the second wavelength band such that the total attenuation factor for the pulse sequence, the second wavelength band, and the gaseous compound has a second value, and such that the total attenuation factor for the pulse sequence, the second wavelength band, and the gaseous compound depends on the temperature in a second way;
selecting the third wavelength band such that the total attenuation factor for the pulse sequence, the third wavelength band, and the gaseous compound has a third value, and such that the total attenuation factor for the pulse sequence, the third wavelength band, and the gaseous compound depends on the temperature in a third way, wherein
the first way is different from the second way, and
the second value is different from the third value; and
determining the temperature and the molecular number density of the gaseous compound as a function of the distance.

8. The method of claim 1, further comprising:
selecting a further wavelength band using information on the spectrum of the absorption coefficient of a further gaseous compound;
generating the pulse sequence also for the further wavelength band;
measuring, as a function of time, the intensity of the scattered light at the further wavelength band;
determining information indicative of the differential absorption between at least two pairs of wavelengths bands selected from the at least four wavelength bands using the measured intensities; and
determining the temperature, the molecular number density, and/or the pressure of the further gaseous compound as a function of the distance using the information indicative of the differential absorption between the further wavelength band and another wavelength band.

9. The method of claim 1, wherein
the temperature of the gaseous compound is at least 400° C.

10. The method of claim 9, wherein the temperature of the gaseous compound is at most 1200° C.

11. The method of claim 1, further comprising:
guiding the pulse sequence in a first direction;
generating, for a first wavelength band and a second wavelength band, a further pulse sequence comprising a light pulse or light pulses;
guiding the further pulse sequence into the thermal device in a second direction, wherein the second direction forms an angle with the first direction, whereby
molecules of the gaseous compound absorb at least part of the light pulse or at least part of the light pulses of the further pulse sequence, and
particles of the gaseous mixture scatter at least part of the light pulse or at least part of the light pulses of the further pulse sequence at various moments of time at least to produce further scattered light;
measuring, as a function of time, the intensity of the further scattered light at the first wavelength band;
measuring, as a function of time, the intensity of the further scattered light at the second wavelength band;
determining information indicative of the differential absorption between the two wavelengths bands using the intensities of the further scattered light; and
determining the temperature and the molecular number density of the gaseous compound as a function of the distance using the information indicative of the differential absorption between the two wavelengths bands for the further scattered light.

12. The method of claim 11, further comprising:
generating multiple pulse sequences;
guiding the multiple pulse sequences into the thermal device in different directions, at least one pulse sequence to a direction; and
determining the temperature and the molecular number density of the gaseous compound as a function of the distance in the different directions, using statistical means, thereby obtaining a two-dimensional or a three-dimensional profile of the temperature and the molecular number density.

13. A method for controlling a thermal process, the method comprising:
determining the temperature and the molecular number density of the gaseous compound as a function of the distance according to the method of the claim 1;
providing information indicative of the temperature and the molecular number density; and
controlling the thermal process using the information indicative of the temperature and the molecular number density.

14. A thermal system comprising:
a thermal device comprising at least a member limiting a space, the member having an optical inlet, wherein, in use, the space is arranged to contain some gaseous mixture comprising some gaseous compound and scattering particles, the gaseous molecules of the compound absorbing at least some light at least at a first wavelength band, a second wavelength band, or a third wavelength band and the scattering particles scattering at least some light at least at the first wavelength band, the second wavelength band, or the third wavelength band;
a light pulse source arrangement arranged to generate, for the first wavelength band, the second wavelength band, and the third wavelength band, a pulse sequence comprising a supercontinuum light pulse or light pulses, wherein the light pulse source arrangement comprises a supercontinuum light pulse source;
means for guiding the pulse sequence into the space through the optical inlet, whereby molecules of the gaseous compound absorb at least part of at least one of the light pulses and the particles of the gaseous mixture scatter at least part of the light pulse or at least part of the light pulses to produce scattered light;
a detector arrangement arranged to measure, as a function of time, the intensity of the scattered light at the first wavelength band, at the second wavelength band, and at the third wavelength band; and
a processing unit arranged to determine at least the temperature and the molecular number density of the gaseous compound as a function of the distance using the measurement results of the detector by determining information indicative of the differential absorption between two pairs of the wavelength bands using the information provided by the detector arrangement.

15. The thermal system of claim 14, wherein
the member or another member limiting the space of the thermal device comprises heat exchange pipes to recover heat from the member by convection, and/or
a linear size of the space is from 2 m to 50 m.

16. The thermal system of claim 14, wherein the detector arrangement comprises:
a beam splitter arranged to divide at least a part of the scattered light to a first part comprising light corresponding to the first wavelength band and to a second part comprising light corresponding to the second wavelength band.

17. The thermal system of claim 14, further comprising:
a reflector for guiding the pulse sequence to the gaseous mixture, wherein
at least an angle of the reflector is arranged to be changeable, whereby the direction into which the pulse sequence is guided is arranged to be changeable.

18. The thermal system of the claim 14, comprising further comprising:
a controller, wherein the processing unit is arranged to provide information indicative of the temperature and the molecular number density of the gaseous compound; and
means for providing the information indicative of the temperature and the molecular number density to the controller, wherein the controller is arranged to control a flow into or out of the thermal device using the information provided by the processing unit.

* * * * *